(12) United States Patent
Korth et al.

(10) Patent No.: US 7,259,246 B2
(45) Date of Patent: Aug. 21, 2007

(54) IMMUNOLOGICAL DETECTION OF PRIONS

(75) Inventors: Carsten Korth, Duesseldorf (DE); Beat Stierli, Daenikon (CH); Peter Streit, Zurich (CH); Bruno Oesch, Stilli (CH); Markus Moser, Pfaeffikon (CH)

(73) Assignee: Universitat Zurich, Zurich (CH)

( * ) Notice: Subject to any disclaimer, the term of this patent is extended or adjusted under 35 U.S.C. 154(b) by 183 days.

(21) Appl. No.: 10/867,589

(22) Filed: Jun. 15, 2004

(65) Prior Publication Data

US 2006/0025575 A1 Feb. 2, 2006

Related U.S. Application Data

(63) Continuation of application No. 09/380,015, filed as application No. PCT/EP98/00917 on Feb. 18, 1998, now Pat. No. 6,765,088.

(30) Foreign Application Priority Data

Feb. 21, 1997 (EP) .................................. 97102837

(51) Int. Cl.
*C07K 16/00* (2006.01)
(52) U.S. Cl. .................................................. 530/388.1
(58) Field of Classification Search ...................... None
See application file for complete search history.

(56) References Cited

U.S. PATENT DOCUMENTS 5,846,533 A * 12/1998 Prusiner et al. .......... 424/130.1

OTHER PUBLICATIONS

Korth et al., Prion (PrpSc)-specific epitope defined by a monoclonal antibody. 1997, Nature vol. 390, p. 74-77.*
Reilly et al., Problems of delivery of monoclonal antibodies. 1995, Clinical pharmacokinetics. vol. 28, p. 126-142.*
Coulthart et al., Variant Creutzfeldt-Jakob disease: a summary of current scientific knowledge in relation to public health. 2001, CMAJ, vol. 165, p. 51-58.*
Irani et al., Diagnosis and prevention of bovine spongiform encephalopathy and variant Creutzfeldt-Jacob disease. 2003, vol. 54, p. 305-319.*
Georgieva et al., Prion diseases. Antibody-mediated prion prevention. 2002, Experimental pathology. p. 60-63.*
Billeter et al., Prion protein NMR structure and species barrier for prion dieseases. 1997, vol. 94, p. 7281-7285.*
Cohen, F.E., et al. Structural clues to prion replication. Science (1994) 264, 530-531.
Collinge, J., et al. Prion protein is necessary for normal synaptic function. Nature (1994) 370, 295-297.
Collinge, J., et al. Molecular analysis of prion strain variation and the etiology of a "new variant" CJD. Nature (1996) 383,683-690.
Diener, T.O., et al. Viroids and prions. Proc. Natl. Acad. Sci. U.S.A. (1982) 79, 5220-5224.
Friden, P.M. Receptor-mediated transport of therapeutics across the bloodbrain barrier. Neurosurgrey (1994) 35, 294-298 (Abstract).

Garfin, D.E., et al. Mitogen stimulation of splenocytes from mice infected with scrapie agent. J. Infect. Dis. (1978) 138, 396-400.
Goldmann, W., et al. Different forms of the bovine PrP gene have five or six copies of a short, G-C-rich element within the protein-coding exon. J. Gen Virol. (1991) 72:201-204.
Griffith, J.S. Self-replication and scrapie. Nature (1967) 215, 1043-1044.
Hecker, R., et al. Replication of distinct scrapie prion isolates is region specific in brains of transgenic mice and hamsters. Genes Dev. (1992) 6, 1213-1228.
Hope, J., et al., Fibrils from brains of cows with new cattle disease contain scrapie-associated protein. Nature (1988) 336,390-392.
Jendroska, K., et al. Proteinase-resistant prion protein accumulation in Syrian hamster brain correlates with regional pathology and scrapie infectivity. Neurology (1991) 41, 1482-1490.
Kascsak, R. J., et al. Mouse polyclonal and monoclonal antibody to scrapie-associated fibril proteins. J. Virol (1987) 61, 3688-3693.
Kasper, K.C., et al. Immunological studies of scrapie infection. J. Neuroimmunol (1982) 3, 187-201.
Kennett, R.H. Fusion centriugation of cells suspended in polyethylene glycol. In Monoclonal antibodies. Hybridomas: a new dimension in biological analysis. (New York: Plenum Press) (1980) pp. 365-367.
Kocisko, D.A., et al. Cell-free formation of protease-resistant prion protein. Nature (1994) 370, 471-474.
Krasemann, S., et al. Generation of monoclonal antibodies against human prion proteins in $PrP^{0/0}$-mice Molecular Medicine (1996) 2, 725-734.
Mehlhorn, I., et al. High-level expression and characterization of a purified 142-residue polypeptide of the prion protein. Biochemistry (1996) 35, 5528-5537.
Oesch, B. et al. Prion protein genes: evolutionary and functional aspects. Curr. Top. Microbiol. Immunol. (1991) 172, 109-124.
Oesch, B., et al. A cellular gene encodes scrapie PrP 27-30 protein. Cell (1985) 40, 735-746.
Oesch, B., et al. Properties of the scrapie prion protein: quantitative analysis of protease resistance Biochemistry (1994) 33, 5926-5931.
Pan, K.M., et al. Conversion of alphahelices into beta-sheets features in the formation of the scrapie prion proteins. Proc. Natl. Acad. Sci. U.S.A. (1993) 90 10962-10966.
Prusiner, S.B. Novel proteinaceous infectious particles cause scrapie. Science (1982) 216, 136-144.
Prusiner, S.B. Molecular biology of prion diseases. Science (1991) 252, 1515-1522.
Prusiner, S.B., et al. Ablation of the prion protein (PrP) gene in mice prevents scrapie and facilitates production of anti-PrP antibodies. Proc. Natl. Acad. Sci. U.S.A. (1993) 90, 10608-10612.

(Continued)

*Primary Examiner*—Stacy B. Chen
*Assistant Examiner*—Agnieszka Boesen
(74) *Attorney, Agent, or Firm*—Abelman, Frayne & Schwab

(57) ABSTRACT

The presented invention relates to monoclonal antibodies useful in sensitive and specific immunological assays for the identification of prions in various tissues and body fluids, the production of such monoclonal antibodies by means of immunization of $PrP^{0/0}$ mice by means of a new recombinant fragment of PrP and the use of the antibodies, e.g. for therapeutic and preventive treatments of humans and animals suffering from prion diseases.

5 Claims, 9 Drawing Sheets

OTHER PUBLICATIONS

Riek, R., et al. NMR structure of the mouse prion protein domain PrP(121-321). Nature (1996) 382, 180-182.

Riesner, D., et al. Disruption of prion rods generates 10-nm spherical particles having high alpha-helical content and lacking scrapie infectivity J. Virol. (1996) 70, 1714-1722.

Serban, D., et al. Rapid detection of Creuzfeldt-Jakob disease and scrapie prion proteins. Neurology (1990) 40, 110-117.

Stahl, N., et al. Scrapie prion protein contains a phosphatidylinositol glycolipid Cell (1987) 51, 229-240.

Stahl, N., et al. Structural studies of the scrapie prion protein using mass spectrometry and amino acid sequencing. Biochemistry (1993) 32, 1991-2002.

Takahashi, K, et al. Purification of scrapie agent from infected animal brains and raising of antibodies to the purified fraction. Microbiol. Immunol. (1986) 30, 123-131.

Tobler, I., et al. Altered circadian activity rhythms and sleep in mice devoid of prion protein. Nature (1996) 380, 639-642.

Wells, G.A., et al. The neuropathology and epidemiology of bovine spongiform encephalopathy. Brain Pathol (1995) 5, 91-103.

Will, R.G., et al. A new variant of Creutzfeldt-Jakob disease in the UK (see comments). Lancet (1996) 347,921-925.

Williams, A.E., et al. Characterization of the microglial response in murine scrapie. Neuropathol. Appl. Neurobiol. (1994) 20, 47-55.

Williams, A.E., et al. Monocyte recruitment into the scrapie-affected brain. Acta Neuropathol (1995) 90, 164-169.

Williamson, R.A., et al. Circumventing tolerance to generate autologous monoclonal antibodies to the prion protein. Proceedings of the National Academy of Sciences of the United States of America (1996) 93, 7279-7282.

* cited by examiner

Capture-ELISA and multimeric PrPSc bov. rbPrP   bov rbPrP   bov   rbPrP
brain        brain       brain
6H4          34C9        15B3

BSE   normal

Peptides 59-63 comprising amino acids 149-153 of BoPrP

FIG.7A

Peptides 64-66 comprising amino acids 155-163 of BoPrP

FIG.7B

Peptides 62-65 comprising amino acids 153-159 of BoPrP
Peptides 73-75 comprising amino acids 173-181 of BoPrP
Peptide 102 comprising amino acids 225-237 of BoPrP

FIG.7C

IMMUNOLOGICAL DETECTION OF PRIONS

This application is a continuation of Ser. No. 09/380,015, filed Aug. 23, 1999, now U.S. Pat. No. 6,765,088 which in turn was the U.S. national phase under U.S.C. § 371 of international application number PCT/EP98/00917, filed Feb. 18, 1998.

FIELD OF THE INVENTION

The present invention relates to monoclonal antibodies reacting with certain epitopes of recombinant bovine prion protein, native and denatured normal or disease-specific prion proteins in soluble or insoluble state, stable hybridonia cell lines producing these monoclonal antibodies, recombinant expression vectors for the expression of recombinant bovine prion protein, purified recombinant bovine prion protein, a test kit for the diagnosis of prion diseases, diagnostic methods for the immunological detection of prion diseases, pharmaceutical preparations for the prevention and therapy of prion diseases, a method for clearing biological material from infectious prion proteins, and methods for the production of these materials.

Abbreviation is Used Hereinbefore and Hereinafter are the Following:
BSA bovine setum albumin
BSE bovine spongiform encephalopathy
CSF cerebrospinal fluid
CJD Creutzfeldt-Jakob disease,
ECL enhanced chemiluminescence
EDTA ethylenediaminetetraacetic acid
ELIFA enzyme linked immuno filtration assay
ELISA enzyme linked immuno sorbent assay
Fab fragment of antibody digested with papain
(Fab')2 fragment of antibody digested with pepsin
FFI Fatal Familial Insomnia
GPI-anchor glycolipid-anchor which "ties" PrP to the outside of the cell membrane
GSS Gerstmann-Sträussler-Scheinker disease
H(A)T-medium hypoxyanthine-(aminopterin)-thymidine medium
HEPES hydroxyethyl-piperazineethane sulfonic acid
HPLC high performance liquid chromatography
IgG immunoglobulin G
IPTG isopropyl-β-D-thiogalactoside
mAB monoclonal antibody
MOPS morpholinepropanesulfonic acid
NC nitrocellulose membrane
o/n overnight
PBS phosphate-buffered saline
PCR polymerase chain reaction
prion proteinaceous infectious particle; the infectious agent of prion diseases supposedly consisting at least of $PrP^{Sc}$ and maybe another yet unknown molecule
PrP prion protein, refers to the common amino acid sequence rather than to a distinct conformation of the two prion protein isoforms
$PrP^{0/0}$-mice lacking a functional PrP gene
$PrP^C$ a normal host prion protein of unknown function; apparent molecular weight 33-35 kDa, same amino acid chain, and same glycosylation at two asparagine residues as $PrP^{Sc}$, is after proteinase K treatment fully digested.
$PrP^{Sc}$ the disease-specific, abnormal isoform of $PrP^C$, with the same amino acid chain, apparent molecular weight 33-35 kDa, glycosylated at two asparagine residues, is after proteinase K treatment shortened to a 27-30 kDa C-terminal fragment. Species-specific $PrP^{Sc}$ isoforms term: human $PRP^{Sc}$ (instead of $PrP^{CJD}$), bovine $PrP^{Sc}$ (instead of $PrP^{BSE}$) etc
rbPrP recombinant bovine prion protein (amino acids 25 to 242 of the bovine PrP gene according to Goldmann et al. 1991; with an additional N-terminal methionine) expressed in E. coli comprising the bovine PrP open reading frame except for the N-terminal signal sequence and the C-terminal GPI-anchor sequence, both are cleaved of during cellular processing. Since this protein is not glycosylated it has a molecular weight of 23 kD
RT room temperature
SAF scrapie-associated fibrils, same as rods plaque-like multimeric $PrP^{SC}$ aggregates
SDS sodium dodecyl sulfate
TBST Tris-buffered saline, Tween 20
TMB tetramethylbenzidine Prion diseases are transmissible neurodegenerative diseases of the central nervous system (for review see Prusiner, 1991). They can be transmitted, inherited or occur sporadically and are observed in animals (e.g. bovine spongiform encephalopatly [BSE] in cattle, scrapie in sheep) as well as in humans (Creutzfeldt-Jakob disease, Gerstmann-Sträussler-Scheinker syndrome, Fatal Familial Insomnia, Kuru). Prion diseases have a characteristically long incubation period and, with the onset of clinical symptoms, lead to ataxia, dementia, psychiatric disturbances and sleeplessness before inevitable death occurs. Neuropathological changes include vacuolar degeneration of brain tissue, astrogliosis and amyloid plaque formation. In the infected subjects, neither a systemic immune response, nor an obvious specific immune response like antibody production to PrP has been observed (Kasper et al., 1982, Garfin et al., 1978) however, some unspecific activation of immune cells in the brain was reported (Williams et al., 1995; Williams et al., 1994).

The infectious agent appears to exist in a variety of strains, which cause distinct incubation times and histopathology (Bruce et al., 1994; Hecker et al., 1992). Transmission of prion diseases is possible between species and most easily within the same species (Prusiner, 1991).

The infectious agent, the prion, is associated with a disease-specific protein, $PrP^{Sc}$, that is an abnormal isoform of a host protein, $PrP^C$ (Oesch et al., 1985, Basler et al., 1986). Both, $PrP^{Sc}$ and $PrP^C$, have an apparent molecular weight of 33-35 kDa on SDS-polyacrylamide gels. They have the same amino acid sequence and are glycosylated at two asparagine residues (Oesch et al. 1985) After proteinase K treatment, $PrP^{Sc}$ is shortened to a characteristic 27-30 kDa fragment while $PrP^C$ is fully digested (Bolton et al. 1982 Oesch et al. 1985). this led to the conclusion that the disease-specific isoform $PrP^{Sc}$ is partially protease resistant while the normal host isoform $PrP^C$ is not Studies on the synthesis and localization of the two PrP isoforms in cultured cells have shown that $PrP^C$ is attached to the cell surface by a glycosyl phosphatidylinositol (GPI) anchor while $PrP^{SC}$ intracellularly within cytoplasmic vesicles (Stahl et al. 1987). Another difference between $PrP^C$ and $PrP^{Sc}$ is reflected in their three-dimensional structure $PrP^{Sc}$ has less alpha helical secondary structures and increased beta sheet content as compared to $PrP^C$ (Pan et al., 1993). So far, no chemical differences between the two isoforms have been observed (Stahl et al., 1993). In summary, $PrP^{Sc}$ and $PrP^C$ have the same amino acid sequence but a different folding. The misfolded prion protein is associated with infectivity and neurotoxicity.

The infectious agent is inactivated by treatments which denature proteins while reagents destroying nucleic acids have no effect (Diener et al., 1982; Alper at al., 1978). In addition, no single nucleic acid capable for coding a protein has been purified until date (Riesner et al., 1993). This has lead to the hypothesis that PrP$^{Sc}$ itself might comprise the infectious particle (Griffith, 1967; Prusiner, 1982). According to this hypothesis, replication of infectivity is achieved by the replication of the pathogenic conformation. It is supposed that infectious PrP$^{Sc}$ molecules convert the normal host protein PrP$^C$ to the PrP$^{Sc}$ conformation (Cohen et al., 1994). Conversion of PrP$^C$ to PrP$^{Sc}$ was claimed to have been achieved in vitro therby mimicking species and strain characteristics comparable to the conversion dynamics in vivo (Kocisko et al., 1994; Bessen et. al., 1995). However, these in vitro converted PrP$^{Sc}$ molecules have, to date, not shown to be infectious.

The function of the normal host protein, PrP$^C$, is unknown. Mice devoid of PrP$^C$ are viable and show no obvious signs of neurological and physical impairment (Bueler et al., 1992) In addition, these mice are not susceptible to infection with prions, underlining the central importance of PrP in the replication of infectivity and/or pathology of these diseases (Bueler et al., 1993, Prusiner et al., 1993). More subtle investigations of PrP knockout mice revealed impaired synaptic function (Collinge el al., 1994) and altered sleep regulation (Tobler at al. 1996). However, a molecular function of PrP$^C$ could not be deduced from these findings.

Prion diseases have gained public interest with the appearance of BSE in the early eighties in Great Britain (Hope et al. 1988), for review see (Wells and Wilesmith, 1995). The disease is supposed to have been transmitted by feeding prion-contaminated meat and bone meal to cattle. It is thought that BSE prions originated from scrapie-diseased sheep by crossing the species barrier from sheep to cattle. BSE has caused an epidemic of considerable importance for both, public health and cattle-dependent economy. Remarkably, no diagnostic method suitable for mass screening of infected tissues of cattle has been developed to date.

Initial diagnosis of prion diseases classically relies on the appearance of clinical symptoms. A definitive diagnosis is made by the observation of neuropathological changes in the medulla oblongata. In few cases, BSE has been shown to be transmissible to other cattle, sheep, pigs and mice. Modern diagnosis additionally uses immunological detection of PrP$^{Sc}$ in brain sections. Since PrP$^{Sc}$ can be detected in the CNS after half of the incubation time in experimentally infected laboratory animals (Jendroska et al., 1991, Hecker et al., 1992), it may serve as an early marker of infection. Hence, specific and sensitive detection of PrP$^{Sc}$ allows the identification of infected animals at a subclinical stage and will help to reduce possible human health risks. By autumn 1996, the BSE epidemic has killed over 160,000 cows in Great Britain alone. In the absence of a diagnostic test, only cattle with clinical symptoms were sorted out from being further processed, allowing a great number of BSE-infected cattle to enter the human food chain (Anderson et al., 1996). This lead to the suspicion that the appearance of a new variant of Creutzfeldt-Jakob disease in Great Britain was caused by transmission of BSE to humans (Will et al., 1996, Collinge et al., 1996). A sensitive detection method for bovine PrP$^{Sc}$ will allow the identification and removal of subclinical BSE-cases from the human food chain.

Oesch et al. (1994) have used a procedure that allows to quantitate the disease-specific isoform of PrP in hamsters. The procedure is based on an ELIFA (enzyme-linked immuno-filtration assay), and is adapted to the particularities of the prion protein, especially the poor solubility of the disease-specific isoform that has made application of conventional ELISA techniques difficult. This procedure (described in detail below) allows for testing of thousands of samples and is thus appropriate for routine screening of animals and humans for prion diseases.

Tagliavini et al. (WO 93/13432) describe a method for detecting soluble prion polypeptides. The drawback of this method is that the inventors claim to detect prion polypeptides that are soluble in vivo, however, it is known since a long time that the disease-associated prion protein PrP$^{Sc}$ is insoluble in vivo. State of the art is that insoluble PrP$^{Sc}$ has to be solubilized in vitro to be detected by immunological methods. Tagliavini et al state (page 3, row 31) "such truncated scrapie proteins have not been found to exist in vivo in substantially soluble form" Furthermore, the inventors give an example wherein they show soluble prion polypeptide fragments in the cerebrospinal fluid (CSF) of patients that do not suffer of the human prion disease CJD but of other unrelated diseases. However, the inventors do not show in vivo soluble protease-resistant prion polypeptides which would prove their hypothesis about the existence of disease-specific prion polypeptides in CSF. In addition, to show prion polypeptides in CSF they use an immunoblot (Western blot); this technique is not appropriate to detect naturally occuring soluble prion polypeptides, since the immunoblot technique requires solubilization of proteins in vitro prior to gel electrophoresis. This procedure would then solubilize even insoluble prion polypeptides that would be suspended in CSF.

Major shortcomings for the immunological detection of PrP have been the unavailability of excellent antibodies able to detect the native disease-specific prion protein (Kascsak et al., 1987; Barry and Prusiner, 1986; Takahashi et al., 1986; Barry et al., 1986). In particular, native PrP$^{Sc}$ was invisible to antibodies (Serban et al., 1990). Furthermore, no monoclonal antibodies recognizing the bovine PrP were available. The reason for the difficulties in raising monoclonal as well as polyclonal antibodies is the highly conserved amino acid sequence of PrP in mammals which apparently prevents an antibody response against most epitopes.

Kascsak et al., (1987) describe the monoclonal antibody 265K3F4 produced by hybridoma cell line ATCC HB 9222 directed against scrapie-associated fibril proteins. The drawback of this method is that by immunizing wild-type mice with PrP, due to self-tolerance, an antigenic reaction against many epitopes is suppressed. The inventors immunized wilde-type mice with purified scrapie-associated fibrils (SAF), SAF are multimeric complexes consisting of PrP$^{Sc}$ that are purified by a ultracentrifugation. The inventors describe an antibody, termed 3F4 that binds only to hamster and human PrP. Furtheron, the antigen has to be denatured either by formic acid or SDS to be detected. It is stated (Kascsak et al. 1987) that the 3F4 antibody binds to undernatured SAF 10-fold weaker than to formic acid denatured SAF. However, the 3F4 antibody does not distinguish between PrP$^C$ and PrP$^{Sc}$.

Williamson et al (1996) have tried to circumvent the lack of an immune response to a highly conserved protein by immunizing transgenic mice lacking PrP (PrP$^{0/0}$-mice) with PrP, however, without success. These authors state that after immunizing PrP$^{0/0}$-mice with PrP "killing these mice for hybridoma production has repeatedly yielded hybridoma cells that failed to secrete anti-PrP antibodies beyond a period of 48h". They presume that during the 48 hours after the fusion anti-PrP antibody-secreting clones either are suppressed to secrete further antibodies or die because of an interaction of the secreted antibodies with cell-resident PrP.

Williamson et al tried to circumvent this problem by isolating antibody-coding RNA and constructing recombinant antibodies by the phage display technique. They obtained several recombinant antibodies which bind to non-denatured mouse prion rods (PrP$^{Sc}$) in the ELISA technique, however, much weaker than to denatured rods and only if substantial amounts of rods were bound to the wells (0.2 µg/well incubated with 5 µg/ml antibody). However, these recombinant antibodies do not detect native PrP$^{Sc}$ in non-denatured histoblots. Thus, the necessity of purifying PrP$^{Sc}$ before antibody detection complicates the use of their immunological detection method.

Krasemann et al. (1996) have made monoclonal antibodies by means of immunizing PrP$^{0/0}$-mice. After DNA-immunization by injecting the DNA coding for the human prion protein directly into a regenerating muscle the mice were subsequently boosted with Semliki Forest Virus particles containing recombinant human prion protein. The authors present hybridoma cell lines producing monoclonal antibodies that bind to the native and denatured normal human prion protein. The binding of these antibodies to the native or denatured disease-specific prion protein, however, is not demonstrated. Furtheron, the obtained antibodies bind to a peptide ELISA system, however an ELISA to normal or disease-specific prion protein is not shown.

We are now the first to show that immunization of PrP knockout mice with highly purified recombinant PrP followed by fusion of splenocytes from these mice with myeloma cells resulted in hybridoma cell lines that secrete highly specific antibodies to both PrP isoforms (PrP$^C$ and PrP$^{Sc}$) in their native as well as denatured state. On the basis of these antibodies, highly specific immunological testing for prion disease was developed.

OBJECT OF THE INVENTION

It is an object of the present invention to overcome the drawbacks and failures of prior art and to provide monoclonal antibodies from stable hybridoma cell lines which can be used in the diagnosis and therapy of prion diseases.

SUMMARY OF THE INVENTION

Surprisingly the drawbacks of the prior art can be overcome by immunization of PrP$^{0/0}$ knockout mice with highly purified recombinant PrP followed by fusion of splenocytes from these mice with myeloma cells. The resulting hybridoma cell lines are surprisingly stable and secrete highly specific antibodies to both PrP isoforms (PrP$^C$ and PrP$^{Sc}$) in their native as well as denatured state. The obtained antibodies are very useful for the development of highly specific immunological tests for prion diseases and other purposes.

The present invention concerns a monoclonal antibody or a fragment thereof capable of specifically binding to recombinant bovine prion protein, and native and denatured normal PrP$^C$ or disease-specific prion protein PrP$^{Sc}$ in an antigen-antibody complex.

The present invention concerns further an antibody or a fragment thereof capable of specifically binding to the binding region (idiotype) of said antibody.

The present invention concerns further a hybridoma cell line capable of producing a monoclonal antibody capable of specifically binding to recombinant bovine prion protein, and native and denatured normal PrP$^C$ or disease-specific prion protein PrP$^{Sc}$ in an antigen-antibody complex.

The present invention concerns further a recombinant expression vector for the expression of recombinant bovine prion protein.

The present invention concerns further a highly purified recombinant bovine prion protein, which may be in reduced or oxidized form.

The present invention concerns further a method for the production of an antibody as mentioned above, comprising culturing a hybridoma cell line as mentioned above and isolating the monoclonal antibody from the supernatant.

The present invention concerns further a method for the production of a hybridoma cell line as mentioned above, comprising administering to PrP$^{0/0}$ mice (knockout mice without a functional PrP gene) an immunizing amount of recombinant prion protein as mentioned above, removing the spleen from the immunized mice, recovering splenocytes therefrom fusing the latter with P3X63Ag8U 1 hybridoma cells ATCC CRL 1597, growing the cells in a selection medium, screening the cells with recombinant PrP and isolating the positive cells.

The present invention concerns further a method for the production of an expression vector as mentioned above, comprising amplifying DNA from bovine genomic DNA coding for PrP by means of N- and C-terminal primers, and inserting the amplified DNA coding for PrP in the correct reading frame into an expression vector.

The present invention concerns further a method for the production of recombinant bovine prion protein comprising culturing microorganisms or cell lines with an expression vector as mentioned above in an appropriate culture medium and isolating and purifying the recombinant protein.

The present invention concerns further a test kit for the diagnosis of prion diseases.

The present invention concerns further an immunological detection procedure for the diagnosis of disease-specific prion proteins.

The present invention concerns further a pharmaceutical preparation for the therapy and prevention of prion diseases comprising a monoclonal antibody as mentioned above and pharmaceutical carrier.

The present invention concerns further a method for the therapy of prevention of prion diseases comprising administering to a patient suffering from such disease or being likely to becoming a victim of this disease a therapeutical or preventive amount of a monoclonal antibody as mentioned above.

The present invention concerns further a method for clearing biological material from prions comprising treating said material with a monoclonal antibody as mentioned above.

b. Western blot of different tissue homogenates from normal cattle. PrP in white blood cells is recognized by the mAB 34C9.

Figure 2:
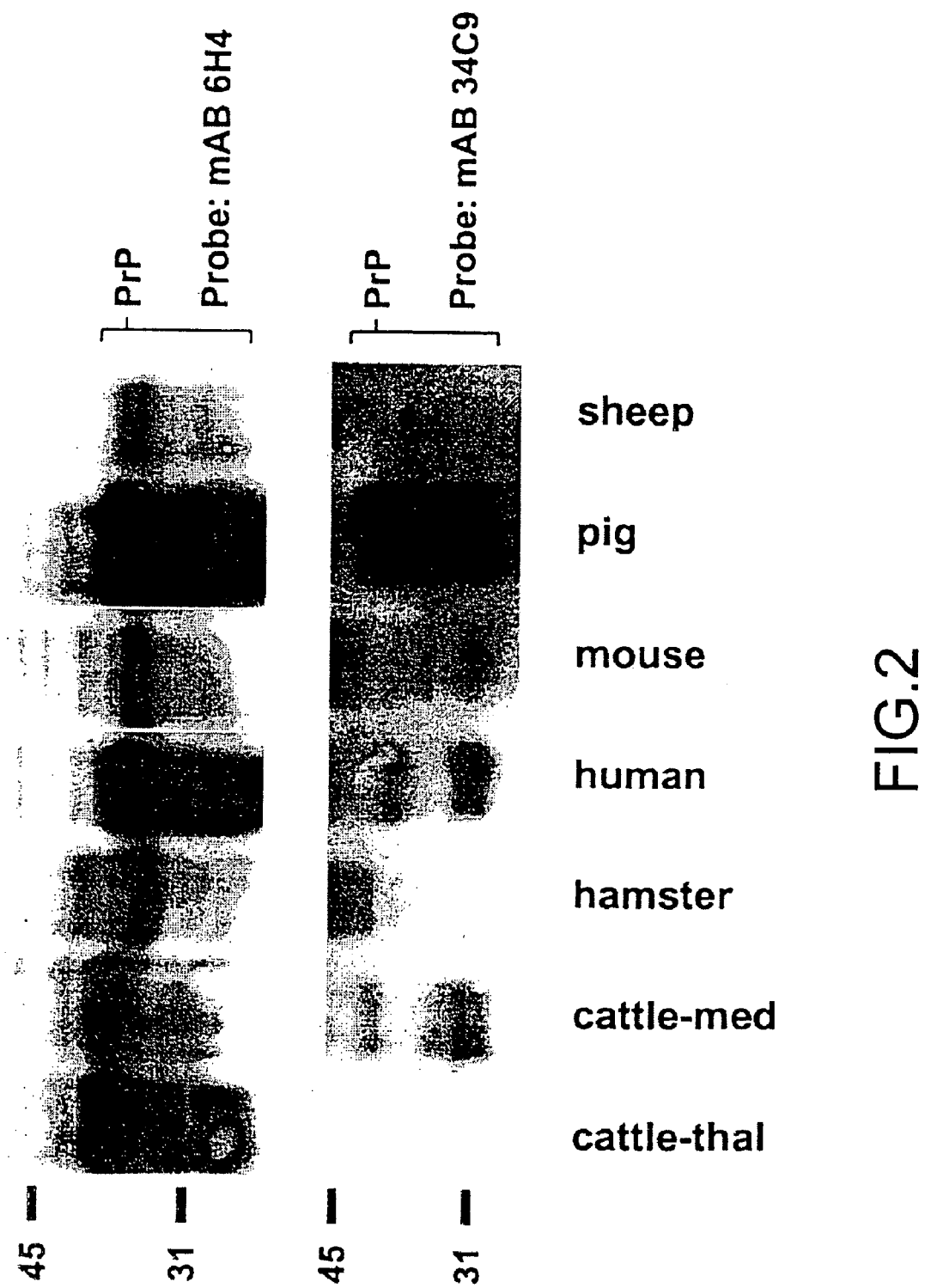

FIG. 2. Western blots of brain homogenates from different species.

a: mAB 6H4 stains PrP of all depicted species, b: mAB 34C9 does not stain PrP from hamster and sheep; mouse PrP staining is weak. This differential staining is consistent with the sequence homology of the mapped epitopes of PrP from different species.

Figure 3A:
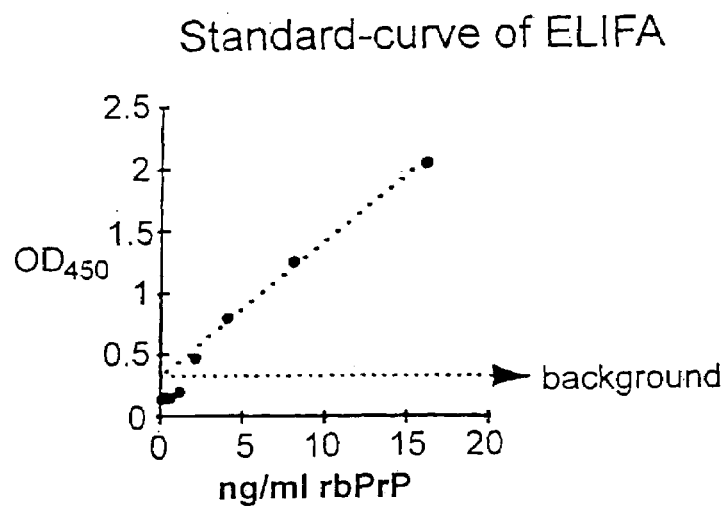

FIG. 3. a. ELIFA standard curve. The standard curve shows a linear relation between the concentration of recombinant bovine PrP and the $OD_{450}$ with a background below 0.5 ng/ml rbPrP. Detection was with mAB6H4.

b. Results ELIFA. Both, the brain homogenates from normal and BSE-diseased cattle have high total amount of PrP as measured by the $OD_{450}$. However, while in BSE-brain there is a substantial amount of protease K-resistant $PrP^{Sc}$, no such PrP can be detected in normal brain.

c. Results ELISA. Both, the brain homogenates from normal and BSE-diseased cattle have high total amount of PrP as measured by the $OD_{450}$. However, while in BSE-brain there is a substantial amount of protease K-resistant $PrP^{Sc}$, no such PrP can be detected in normal brain.

Figure 4A:
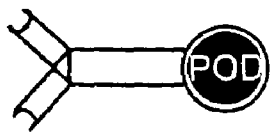
Figure 4B:
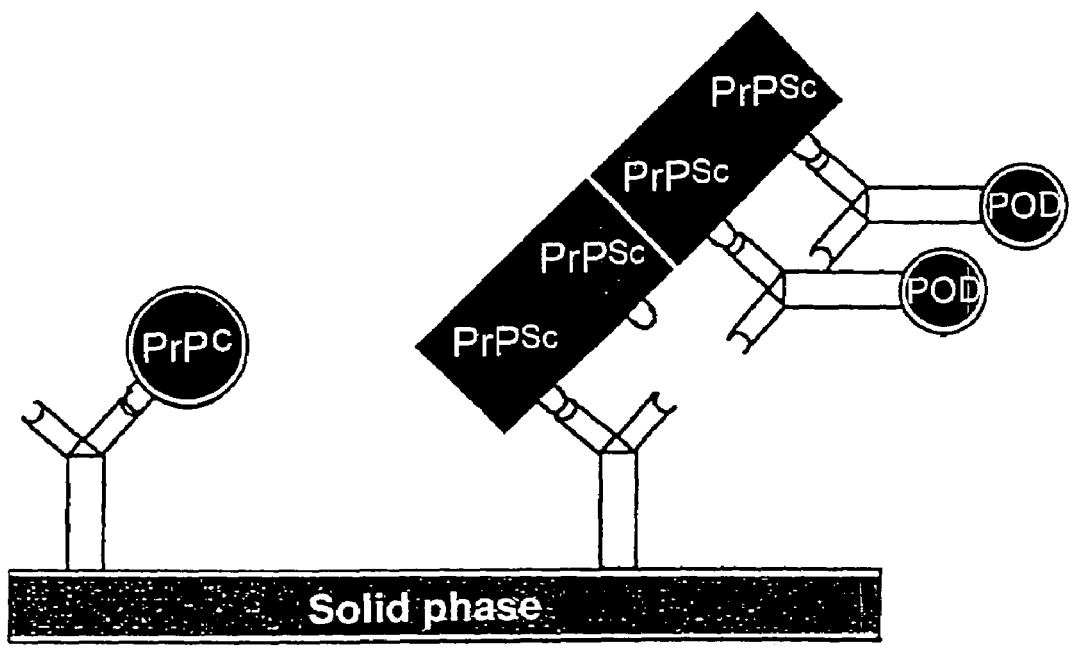

Empty column without proteinase K treatment
black column after proteinase K treatment FIG. 4. Scheme capture ELISA and multimeric $PrP^{Sc}$ See also text a monomeric $PrP^C$ has no additional binding sites since the only binding site is occupied by the coating antibody b multimeric disease-specific $PrP^{Sc}$ has additional binding sites for the detecting, peroxidase-labeled mAB 6H4 (POD) or 15B3 (POD)

Figure 5:
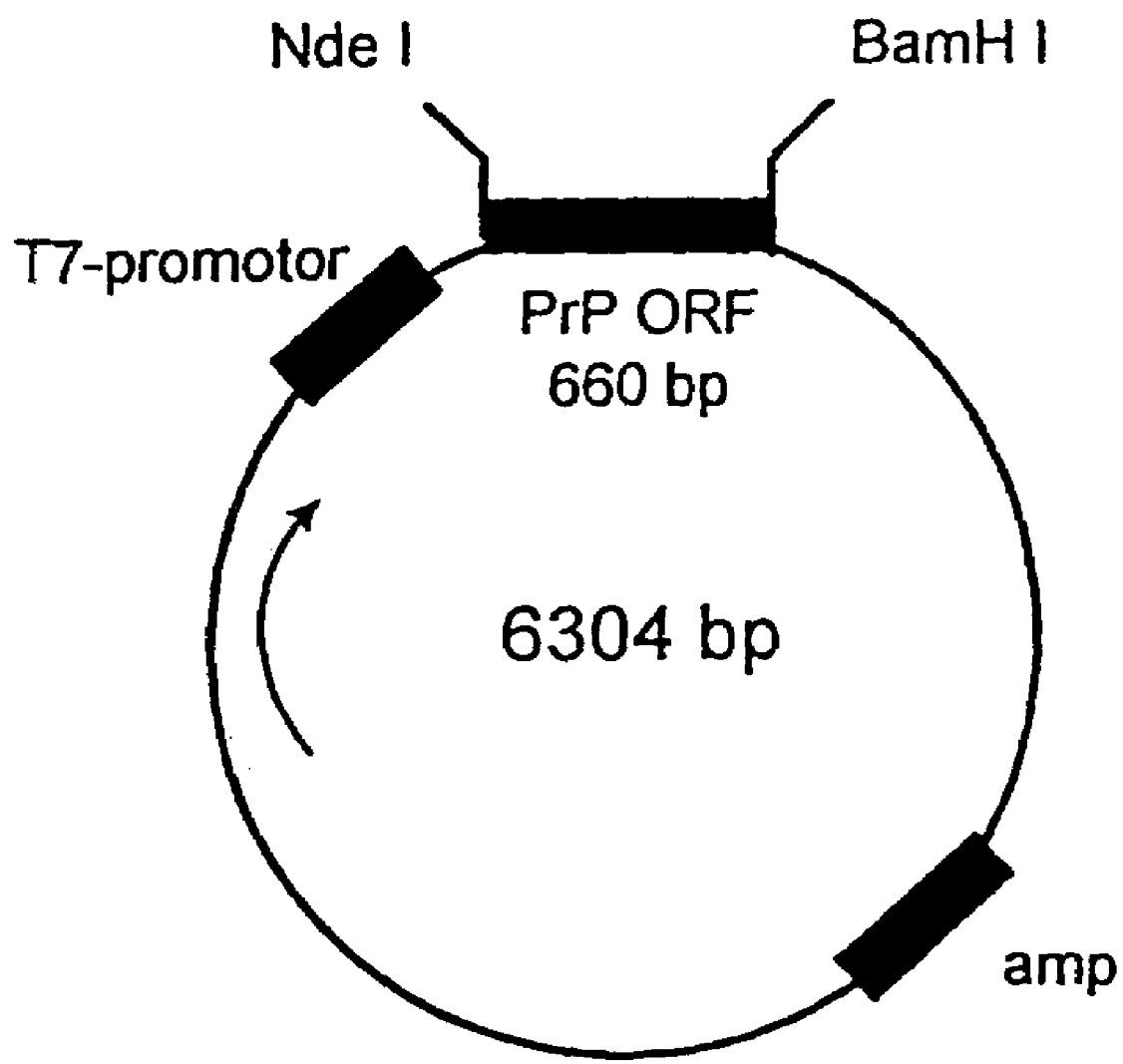

FIG. 5. Schematic map of plasmid pbPrP3. The insert PrP ORF corresponds to SEQ ID NO 1 with the restriction sites Nde I and BamHI.

FIG. 6. a. Western blots of normal bovine brain homogenates and recombinant bovine PrP mABs 6H4 and 34C9 recognize both bovine PrP and rbPrP, whereas mAB 15B3 recognizes only rbPrP. Recombinant rbPrP runs lower and sharper than PrP from brain homogenates because it is not glycosylated.

b. Conformation-sensitive ELIFA of brain homogenates from BSE-diseased and normal cattle at different denaturation states. Staining with monoclonal antibody 15B3. In the native state, mAB 15B3 stains only bovine $PrP^{Sc}$, and not $PrP^C$.

FIG. 7. Epitope mapping on the peptide library for bovine PrP:

a: mAB 34C9 recognizes peptides Nos. 59 to 63 of the peptide library comprising the epitopes of amino acids 149 to 153 (Leu Ile His Phe Gly; SEQ ID NO 5) of bovine PrP according to Goldmann et al. (1991) corresponding to amino acids 126-130 in SEQ ID NO 2.

b: mAB 6H4 recognizes peptides Nos. 64 to 66 of the peptide library comprising the epitopes of amino acids 155 to 163 (Asp Tyr Glu Asp Arg Tyr Tyr Arg Glu, SEQ ID NO 6) of bovine PrP according to Goldmann et al. (1991) corresponding to amino acids 132-140 in SEQ ID NO. 2.

c: mAB 15B3 recognizes 3 distinct arrays of peptides: Nos. 62 to 65 of the peptide library comprising amino acids 153 to 159 (Gly Ser Asp Tyr Glu Asp Arg, SEQ ID NO 7), Nos. 73 to 75 comprising amino acids 173 to 181 (Tyr Tyr Arg Pro Val Asp Gln Tyr Ser. SEQ ID NO 8) and No. 102 comprising amino acids 225 to 237 (Cys Ile Thr Gln Tyr Gln Arg Glu Ser Gln Ala Tyr Tyr: SEQ ID NO 9) of bovine PrP according to Goldmann et al (1991)

FIG. 8. Immunoprecipitation of bovine, mouse and human PrP with monoclonal antibodies 15B3 and 6H4 a. The supernatant of a centrifuged homogenate from the medulla of two different BS-diagnosed or two normal animals was incubated with antibodies 6H4 or 15B3. Antibodies were precipitated with protein A (15B3) of protein G-agarose (6H4). As a control, protein A only was incubated without antibodies. Precipitates were analysed on a western blot for the presence of PrP using a polyclonal rabbit antiserum to bovine PrP and goat-anti-rabbit Ig coupled to alkaline phosphatase. Signals were developed with chemiluminscence substrates. Crossreaction of the secondary antibody with immunoprecipitated mouse immunoglobulins leads to the prominent band at about 50K. Note the 50 K band characteristic for $PrP^{Sc}$ in the 15B3 but not in the 6H4 immunoprecipitations b. Proteinase K digestion of $PrP^{BSE}$ immunoprecipitated with mA 15B3. Undigested and digested bovine brain homogenates were compared to proteinase K digested immunoprecipitates with protein A-agarose only or with 15B3. The sharp band at 31K represents a crossreactivity of the secondary antibody with proteinase K. The same immunoprecipitates and method of analysis were used as in a. c. Immunoprecipitation of mouse $PrP^{Sc}$ with mAB 15B3. Homogenates from PrP-null mice (0/0) or wild-type mice (normal (*/*) or scrapie infected (+/+Sc)) were immunoprecipitated with mAB 15B3 or protein A-agarose only and analysed by western blotting as described. Digestion with proteinase K after (a) or before (b) the immunoprecipitation is indicated. Detection of PrP was done as described. d. Immunoprecipitation of human $PrP^{CJD}$ with mAB 15B3. Brain homogenates (cerebellum) from normal persons or CJD patients type 1 (ref 10) were immunoprecipitated and analysed as described for a. Two representative examples from a total of 4 normal persons and 4 CJD cases are shown.

SEQ ID NO 1 shows the 660 base pair sequence encoding the bovine PrP obtained from genomic bovine DNA by PCR amplification SEQ ID NO 2 shows the amino acid sequence of recombinant bovine rPrP which comprises amino acids 25 to 242 of the bovine PrP open reading frame (Goldmann et al., 1991).

SEQ ID NO 3 shows the N-terminal sense primer, and

SEQ ID NO 4 shows the C-terminal antisense primer. These primers comprise a Nde 1 restriction site at the 5'-end and a BamHI restriction site at the 3'-end in the PCR-amplified bovine PrP-DNA.

SEQ ID NO 5 shows the amino acid sequence common to peptides 59 to 63 of the peptide lybrary recognized by mAB 34C9.

SEQ ID NO 6 shows the amino acid sequence common to peptides 64 to 66 of the peptide lybrary recognized by mAB 6H4.

SEQ ID NO 7 shows the amino acid sequence common to peptides 62 to 65 of the peptide lybrary being the first of 3 partial sequences recognized by mAB 15 B3.

SEQ ID NO 8 shows the amino acid sequence common to peptides 73 to 75 of the peptide lybrary being the second of 3 partial sequences recognized by mAB 15 B3.

SEQ ID NO 9 shows the amino acid sequence common to peptide 102 of the peptide lybrary being the third of 3 partial sequences recognized by mAB 15 B3.

DETAILED DESCRIPTION OF THE INVENTION

In the following detailed description the spirit and scope of the invention will become more clearly explained and understood.

The Monoclonal Antibodies

A monoclonal antibody according to the invention is intended to bind to, to detect and qualitatively and quantitatively measure the presence of epitopes of prion proteins whether they are in soluble or insoluble form in various tissue specimens such as homogenates or sections of brain, spleen, tonsils, white blood cells or others and body fluids such as blood, cerebrospinal fluid saliva, urine or others. The present mABs bind to epitopes of amino acids in a row or to epitopes of amino acids on different loops of the three-dimensional struture of native PrPs which are spatially close to each other. A particular group of the present antibodies binds only to native disease-specific PrP and not to native normal PrP.

Any known mABs which would fall under these definitions are exempted and disclaimed.

The term monoclonal antibody comprises also chimeric monoclonal antibodies having similar properties, which are derived from different animals, such as human/mouse chimeric antibodies or any other chimeric molecule comprising the antigen-binding part of the monoclonal antibody (idiotype) with other molecules such as antibody fragments of other monoclonal antibodies or enzymes.

A fragment of a monoclonal antibody comprising the binding part of the monoclonal antibody (idiotype) likewise capable of specifically binding the antigen and is termed Fab or (Fab')$_2$ depending on whether the monoclonal antibody is digested with papain or pepsin, respectively.

A synthetic antibody or fragments thereof designed according to the amino acids or substituted homologous amino acids composing the idiotype responsible for binding the antigen. Homologous amino acids are defined as exchanges within the following five groups. 1. Small aliphatic, nonpolar or slightly polar residues: alanine, serine, threonine, glycine, proline; 2. Polar, negatively charged residues and their amides: aspartic acid, asparagine, glutamic acid, glutamine. 3. Polar, positively charged residues: histidine, arginine, lysine; 4. Large aliphatic, nonpolar residues: methionine, leucine, isoleucine, valine, cysteine; 5. Large aromatic residues: phenylalanine, tyrosine, tryptophan.

Preferred monoclonal antibodies are those named 6H4, 34C9, 15B3 which are produced by hybridoma cell lines DSM ACC2295, DSM ACC2296 and DSM ACC2298, respectively.

The antibodies and fragments thereof are essential tools for immunological detection procedures based on the binding of the prion protein to the presented monoclonal antibodies in an antigen-antibody complex. The monoclonal antibodies of the invention react with recombinant bovine PrP as well as native or denatured PrP$^C$ and PrP$^{Sc}$ whether they are in soluble or insoluble state. The monoclonal antibodies react furtheron with PrP from different species, for example humans, hamsters, pigs, sheep, cattle and mice.

Furthermore, the present antibodies by forming an antigen-antibody complex between the presented monoclonal antibodies and the prion protein can be used to inhibit neurotoxic and infectious properties of the disease-specific prion protein.

Anti-idiotype Antibodies

The invention concerns further anti-idiotype antibodies which are antibodies that bind with their binding region (idiotype) to the binding region of the original monoclonal antibody. The anti-idiotype antibody mimicks features of the original antigen, in this case features of PrP. Anti-idiotype antibodies are raised as polyclonal antibodies (serum) or monoclonal antibodies from animals immunized with the preferred antibodies according to the invention. Anti-idiotype antibodies are valuable tools in detecting and blocking interactions of the original antigen (PrP), particularly interactions with receptors and can therefore be used in prevention and therapy of prion diseases.

The Hybridoma Cell Lines

A stable hybridoma cell line according to the invention is capable of producing a monoclonal antibody as defined above over a prolonged time period of at least 6 months. Such cell lines are derived from the fusion of a spleen cell expressing the antibody derived from mice lacking a functional PrP gene, and a myeloma cell of mice providing survival of the fused cell line.

Prefered hybridoma cell lines are DSM ACC2295, DSM ACC2296 and DSM ACC2298. The first two cell lines were deposited under the Budapest Treaty on Feb. 06, 1997 at the Deutsche Sammlung von Mikroorganismen and Zellkulturen GmbH, Mascheroder Weg 1b, D-38124 Braunschweig, a recognized public depository for strains of microorganisms. The hybridome cell line producing mAB 15A3 was deposited Feb. 13, 1997 unter number DSM ACC2298 at the same depository.

The Expression Vector for Recombinant Bovine Prion Protein

An expression vector for the expression of the recombinant bovine prion protein is a DNA vector, based on the pET11a vector by Novagen comprising essential sequences for expression in the respective host, e.g. a T7-promotor and the DNA coding for the bovine prion protein from codons 25 to 242 with an additional codon ATG at the 5'-end the PrP-coding DNA and sequence for selecting, eg. the ampicillin gene, multiplication and termination.

Preferred expression vector is pbPrP3 as shown in FIG. 5.

The Recombinant Bovine Prion Protein

The present recombinant bovine prion protein consists of the amino acid sequency ID No:2. It may be unglycosylated or glycosylated.

The present recombinant bovine prion protein PrP is purified to a homogeneity of >98%. It can be present in oxidized or reduced form. In the oxidized form the single -S-S-bridge is present whereas in the reduced form two SH groups are present instead. The amino acid sequence of the present recombinant bovine PrP is shown in ID No. 2. The protein is glycosylated if expressed in a glycosylating eukaryotic cell line, such as Chinese Hamster cells or unglycosylated if expressed in a procaryotic cell line, such as *Escherichia coli*. Mixtures of oxidized and reduced form are also comprised. The oxidized form has the molecular weight of 23676 8 Da and the reduced form 236886.1 Da as determined by electrospray mass spectroscopy. The present full length recombinant bovine prion protein is unique in terms of its homogenity, since other groups in the art have reported of being unable to purify homogenous full length recombinant prion protein of other species (Mehlhorn et al., 1996 Riek et al., 1996).

The reduced form of the recombinant PrP is particularly interesting since it has been reported to contain more β-sheet secondary structures than the oxidized form (Mehlhorn et al., 1996). hence mimicking structural features of PrP$^{Sc}$. However, the reduced recombinant isoforms have been reported to be neither protease-resistant nor infectious (Mehlhorn et al., 1996).

A native prion protein PrP is the prion protein in a fully folded state, i.e. the three-dimensional structure is present. Only in the native, i.e. folded state PrP isoforms are different (normal native vs. disease-specific native PrP).

A denatured prion protein is the prion protein in the unfolded state. Unfolding is usually achieved by the addition of chaotropic substances such as urea or guanidinium hydrochloride. In the denatured state, both PrP isoforms are irreversibly the same, even if they have been normal native or disease-specific nativ before.

An antigen-antibody complex is a physical attachment of an antibody or fragment thereof with the corresponding antigen by intermolecular forces because the surfaces match in a unique way. The matching surface on the antibody is called idiotype and the surface on the antigen is called epitope.

Suitable epitopes detectable by the present antibodies are for example linear amino acid sequences having from about 3 to about 15 amino acids in a row or are completely three-dimensional ("patch") in that distant amino acid residues of the linear peptide backbone of the protein are, due to the unique folding, very close together in space to form an epitope.

The Method for the Production of an Antibody.

The present method for the production of an antibody according to the invention comprises culturing a hybridoma cell line as mentioned above and isolating the monoclonal antibody from the supernatant of the growth media.

Culturing is carried out in flasks in HT-medium or in a cell culturing system called "technomouse" in serum-free synthetic medium (Turbodoma medium, supplied by Messi, Zurich). In a "technomouse" hybridoma cells are cultured in a sterile chamber surrounded by a protein-impermeable membrane that is perfused by the respective medium in a constant flow rate (for example, turbomedium at 80 ml/h), antibodies are collected from the chamber with the help of a syringe at regular intervals.

Isolation of monoclonal antibodies is carried out by extraction from the supernatant by conventional biochemical methods, e.g. by use of affinity columns with the corresponding immobilized antigen or by any other method used in the art, such as gel filtration or ion exchange chromatography. In the "technomouse" supplied with serum-free turbomedium antibody concentrations and purities are achieved that need no further extracting procedures.

Chimeric antibodies and fragments thereof can be produced by genetic engineering methods, e. g. by sequencing the antibody or the desired fragment thereof and constructing DNAs coding for the chimeric antibody or the fragment thereof which DNAs are inserted into an appropriate expression vector and expressed to produce the antibody or the fragment thereof in both procaryotic or eukaryotic cell lines.

A fragment binding to a PrP epitope can be combined with a human heavy chain to produce chimeric antibodies for use in humans as therapeutic or preventive agents against a prion disease. A fragment binding to a PrP epitope can also be combined with other enzymes, proteins or molecules to give rise to chimeric molecules combining the biological functions of these, for example for targeting an enzymatic activity to a place defined by the proximity of the PrP epitope.

The Method for the Production of a Hybridoma Cell Line

The present method for the production of a hybridoma cell line comprises administering to $PrP^{0/0}$ mice (knockout mice without a functional PrP gene) an immunizing amount of a recombinant pure prion protein PrP, removing the spleen from the immunized mice, recovering splenocytes therefrom, fusing the latter with appropriate myeloma cells, growing the cells in a selection medium which does not support survival of the unfused cells, e. g. in HAT medium, screening the supernatants of the surviving hybridoma cells with recombinant PrP for the presence of antibodies to detect recombinant bovine PrP by an ELISA procedure and to detect native bovine $PrP^{Sc}$ by a conformation-sensitive ELIFA procedure and isolating the positive cells. Positive hybridomas were selected and cloned twice by the limiting dilution method before the antibody was characterized and the epitope was mapped on a peptide library.

The peptide library used is commercially available from Jerini Biotools (Berlin Germany). It consists of 104 spots with peptides of 13 amino acids, whereby the sequence of each peptide overlaps with 11 amino acids of the foregoing peptide.

An immunizing amount of a recombinant bovine prion protein is from about 50 to 100 μg. It is administered dissolved in an appropriate solvent, e. g. PBS and Freund's adjuvant several times, e. g. three times, subcutaneously followed by an intraperitoneal and an intravenous injection ultimately prior to spleen removal.

The $PrP^{0/0}$ mice were a gift from Prof. Weissmann of the University or Zürich. They were obtained according to Büeler et al. (1992).

Appropriate myeloma cell are for example P3X63Ag8U.1 deposited and available under ATCC CRL 1597.

Recovering spleen cells and fusion conditions follow standard procedures, for esample as described by Kennett (1980).

The Method for the Production of an Expression Vector

The method for the production of an expression vector comprises inserting a DNA coding for PrP in the correct reading frame into an expression vector. One of the structures of the DNA coding for PrP is shown by SEQ ID NO:1. This DNA can be obtained by amplifying DNA from bovine genomic DNA coding for PrP by means of the N- and C-terminal primes shown by SEQ ID NO: 3 and SEQ ID NO: 4, respectively. Bovine genomic DNA is isolated from bovine kidney cells and supplied by Clonetech, U.S.A. Degenerate allelic forms of this DNA coding for the same PrP may be used. Furthermore, targeted mutations can be introduced into the PrP DNA to give use to distinct conformational isoforms of the translated gene product.

The Production of a Purified Recombinant Bovine PrP

The production of a purified recombinant bovine PrP comprises culturing a cell line with an expression vector capable of expressing the bovine PrP in an appropriate culture medium, such as in the case of *E. coli* in Luria broil medium, isolating the PrP protein from the inclusion bodies by lysing the cells e. g. with lysozym and Triton-X-100 in the case of *E. coli*, solubilizing the inclusion bodies with urea and and purifying the protein, by conventional methods, e. g. by chromatography, for example on a anionic exchange sepharose column and C4 reverse phase HPLC column.

The oxidized form is obtained by treatment with an oxidizing agent, e. g. with $Cu_2SO_4$, and the reduced form by treatment with a reducing agent, e. g. β-mercaptoethanol, according to conventional methods. They can be separated by reverse-phase high pressure liquid chromatography.

Immunological Detection Procedure for the Detection of Prion Disease

An immunological detection procedure for the detection of prion disease, especially BSE, whereby disease-specific $PrP^{Sc}$ protein in biological material of an animal or human is detected, comprises treatment of a first probe of said material with a monoclonal antibody according to the invention and detecting the mixed $PrP^{C}/PrP^{Sc}$-antibody complex, treating a second probe of said material first with proteinase K and then with the monoclonal antibody according to the invention, detecting the PrP$^{Sc}$-antibody complex and analyzing the results of both probes.

A specific monoclonal antibody according to the invention is able to detect PrP$^{Sc}$ in a PrP$^{Sc}$-antibody complex without prior protease-digestion of the tissue specimen to be examined.

The biological material can be insoluble or soluble in buffer or body fluids. It can be derived from any part of the body, e. g. from the brain or the tissue sections, in which case it is used in form of a homogenate, or any body fluid; e. g. cerebrospinal fluid, urine, saliva or blood. In the case of body fluids, fluid-resident cells, e.g. white blood cells in the case of blood expressing PrP Can be purified and analyzed either in immunohistochemistry or as a homogenate.

The detection of the PrP$^{Sc}$-antibody complex is carried out in particular by immunological procedures like the Western blotting, ELIFA, and various ELISA techniques such as capture ELISA.

The present immunological detection procedures allow the diagnosis of prion diseases. With the tools of the present invention, tissue sections, tissue homogenates or body fluids of prion-infected animals such as BSE-diseased cattle or humans having the CJD can be screened for the presence of the protease-resistant, disease-specific isoform of the prion protein in its native form, be it soluble or insoluble.

Tissue homogenates and body fluids are for example such as from biopsy of brain, lymph nodes, spleens, tonsils, peripheral nerves, cerebrospinal fluids, urine, platelets or white blood cells. Particular immunological procedures comprise for example, enzyme-linked immunofiltration assay (ELIFA), enzyme-linked immunoabsorbent assay (ELISA), Western blot assay, dot blot assay, immunodecoration and immunohistochemistry.

When native bovine PrP$^{Sc}$ or any other disease-specific prion protein (e.g. ovine PrP$^{Sc}$ or human PrP$^{Sc}$) has to be used in immunological assays, this can presently only successfully be achieved with the antibodies described in the present invention, since the present antibodies are the first of their art to be able to bind only native, disease-specific PrP$^{Sc}$.

The Test Kit for the Diagnosis of Prion Diseases

The test kit for the diagnosis of prion diseases comprises devices and materials enabling the diagnosis prion disease in biological materials, and is particularly suited for screening large amounts of samples for the presence of PrP$^{Sc}$. One test kit comprises in particular one or more monoclonal antibodies according to the invention, purified bovine recombinant PrP protein as mentioned above, nitrocellulose sheets, microliter plates, or microliter plates coated with the monoclonal antibodies according to the invention, a secondary anti-mouse antibody that is coupled with an enzyme and its substrate or any other molecular compound for a detection reaction (e.g. a peroxidase-labeled anti-mouse IgG antibody. TMB or any other peroxidas substrate), hydrogen peroxide, proteinase K, a blocking buffer, a homogenization buffer, a calibration curve and a description of how to perform the test.

Another test kit is designed in the dipstick format and is without need of radioactive tracers, enzymes or substrates and basically reduces the number of handling steps to one. The one-step procedure involves the capture of the disease-specific PrP$^{Sc}$ with one of the antibodies according to claim 1 or 2 which are immobilized on a test strip. Captured disease-specific PrP$^{Sc}$ are detected directly by a second antibody according to the invention, which is coupled to particular colloid particles. This specific detector complex results in the formation of coloured spots on the test strip which are visible in less than 30 minutes depending on the concentration of the test sample. The spots are a permanent record of the test result and, upon longer exposure even increase the sensitivity of the test without generating higher background.

Pharmaceutical Preparation for the Therapy and Prevention of Prion Diseases

The pharmaceutical preparation for the therapy and prevention of prion diseases in a mammal, including humans, comprises an effective amount of one or more antibodies fragments therof or chimeric antibodies as described, produced according to the invention, eventually purified according to conventional methods, and a conventional pharmaceutical carrier. An antibody obtained may be solubilized together with the carrier in an appropriate buffer, e. g. an aqueous physiological sodium chloride solution. This may be clarified by centrifugation and used in concentrated liquid form for injection, or completely dried if desired by any of the conventional methods, such as lyophilization, spray or freeze drying, in form of a dry powder, which can be pressed into tablets, filled into capsules, or applied as a dry powder in form of a nasal spray, whereby conventional production methods are applied, and conventional pharmaceutical carriers are optionally added.

Method of Protecting a Mammal Against Prion Disease

The monoclonal antibodies of the present invention bind to between species highly conserved regions in the PrP molecule that may have functional significance (Oesch et al. 1991). It is envisioned that blocking this binding site by the monoclonal antibodies, fragments thereof or chimeric antibodies as defined above will abolish biological effects of prions. Blocking of the infectivity of prions by occupying distinct sites on the disease-specific form of PrP is foreseen to represent a therapeutic strategy in treating prion diseases or a preventive strategy in preincubating suspected prion-infected tissue specimens with the present monoclonal antibodies. The normal form of PrP appears not to be of vital importance in the living animal because mice with a deleted PrP are viable (Bueler et al., 1992) Anti-PrP antibodies may therefore be used without side effects to neutralize prions in humans or animals.

The present invention concerns further a method for the therapy or prevention of prion disease or a disease mediated by the neurotoxic effects of prion proteins or fragments of prion proteins, comprising administering to a patient suffering from such disease or being likely to becoming a victim of this disease a therapeutical or preventive amount of a monoclonal antibody, a fragment thereof or a chimeric antibody as described above.

The method of protecting a mammal, including a human, against an infectious prion disease according to the present invention comprises administering one or a combination of the present antibodies, fragments thereof or chimeric antibodies or a pharmaceutical preparation comprising the antibodies produced by the present invention. The pharmaceutical preparation is preferably administered by injection, e. g. intrathecally (into the cerebrospinal fluid), into the blood with respective pharmaceutical agents or methods increasing the permeability of the blood-brain barrier or as a chimeric antibody, fused to, or containing additional signal sequences that allow passage through the blood-brain barrier (for review see Friden, 1994). An intranasal application of the monoclonal antibodies, fragments or chimeras thereof is also possible.

The pharmaceutical preparations have to be administered according to the judgment of the physician in amounts depending on the concentration of the antibodies comprised thereby and the route of administration so that a protective or curative effect is obtained. The amounts and method of administration are to be selected further depending upon the age and weight of the patient, the nature and severity of the infection as well as the general condition of the patient. In general it is sufficient to administer the antibodies in amounts of about 1 to 100 mg per patient in a single or in repeated doses.

Method for Clearing Biological Material from Prions

The method for clearing biological material from prions, e. g. intended for transplantation, substitution of biological material or oral consumption, comprises treating said material with one or several monoclonal antibodies according to the invention such that prions or prion proteins or fragments thereof become functionally inactivated in terms of their infectivity and/or neurotoxicity. The pharmaceutical preparations described above may be used for this purpose, whereby the pharmaceutical carrier nay be replaced by a suitable other solvent in case the biological material is not intended to be used for transplantation.

The following examples serve to illustrate a particular embodiment of the invention but they should not be considered a limitation thereof. The immunological procedures outlined are made for the diagnosis of BSE in cattle, however, these procedures can also be applied for prion diseases in humans or animals such as sheep, hamsters or mice.

Method for protecting an animal or a human by immunization with recombinant PrP

The method for protecting animals or humans from infection with prions consists of an appropriate formulation of recombinant PrP of the appropriate species with an immunostimulator such as Freund's adjuvans. To protect against BSE, immunization is done with bovine PrP, against CJD human PrP is used, against sheep scrapie sheep PrP is used. In general, the PrP of the species where the the prion originated is used for immunization. Immunization induces the β-lymphocytes to produce antibodies reacting with $PrP^{Sc}$. Such antibodies (of which 15B3 is a prototype) will be present in bood and lymphatic tissue and thereby bind and neutralize prions infecting a human or animal through peripheral pathways such as through skin lesions for example after accidental puncture with a needle or knife in a hospital or a slaughterhouse. The amount and type of PrP to be used for immunization will be determined according to the age and weight of the human or animal as well as the source of prions.

EXAMPLE 1

Immunological Diagnosis of Prion Diseases Using Tissue from Infected Animals $PrP^C$ and $PrP^{Sc}$ can be distinguished according to their different sensitivity to digestion with protease K. Undigested $PrP^C$ and $PrP^{Sc}$ have a molecular weight of 33-35 kDa. Upon incubation with proteinase K $PrP^C$ is readily digested while $PrP^{Sc}$ is partially resistant, i.e. the N-terminus of $PrP^{Sc}$ is removed leading to a shift in molecular weight from 33-35 kD to 27-30 kD (Oesch et al , 1985). Proteinase K is therefore used to digest the tissue specimen to be examined. However, monoclonal antibody 15B3, detecting a conformational epitope specific for the disease-specific isoform $PrP^{Sc}$ may even be used without prior protease digestion.

EXAMPLE 1.1.

Method for the Preparation of Tissue Homogenates

One gram of brain, either from the thalamus, medulla or spinal cord, were homogenized with an homogenizer (Omni, USA) in 10 ml 10% sucrose, 20 mM HEPES pH 7.5, 2% sarcosyl and 5 mM EDTA, 10% homogenates were diluted 10 fold, one part of the homogenate was digested with proteinase K at 0, 10 or 100 μg/ml. The probe containing 0 μg/ml served as a control for the specificity of the proteinase K treatment. Probes were then further diluted (in PBS) for the ELIFA test to give a blotting concentration of 0.05% of brain homogenate. To increase the partial protease resistance of bovine $PrP^{Sc}$, brain homogenates from BSE-infected and normal cattle was diluted after homogenization in 20, 40 or 80% ethanol/HEPES-sucrose buffer. Suspension of brain homogenates in ethanol was an important step and effectively stabilized the β-sheet structure of the $PrP^{Sc}$ isoform (Oesch et al., 1994), thereby increasing its protease resistance (Riesner et al., 1996).

EXAMPLE 1.2.

Western Blotting

Tissue specimens were homogenized as described in example 1.1. one part protease-digested, the other not (as described above), diluted to 10% and separated by SDS polyacrylamide gel electrophoresis (SDS-PAGE) on 12% gels (Sambrook et al, 1989) Gels were electroblotted onto 0.45 μm nitrocellulose (NC) membranes, incubated with the respective monoclonal antibodies followed by a secondary anti-mouse IgG antibody coupled to peroxidase. Bound peroxidase activity was detected with a chemiluminescence kit (ECL, Amersham USA)

Western blots developed with antibodies 6H4 or 34C9 (FIG. 1A) show the characteristic smear of bands for $PrP^C$ and bovine $PrP^{Sc}$ (33 to 27 kD) in undigested probes while digestion with proteinase K eliminates all of $PrP^C$, however, leaving a 27 kD band typical of N-terminally truncated $PrP^{Sc}$. The smear is due to different glycosylated forms or PrP.

The present antibodies were furthermore able to detect PrP in various tissue extracts from humans, cattle, pigs. sheep, mice and hamsters (FIGS. 1B, 2). Given that the epitopes of our antibodies are highly conserved (Oesch et al., 1991), we expect our antibodies to stain PrP from other species such as rat or marsupials as well.

EXAMPLE 1.3

ELIFA (Enzyme Linked Immune Filtration Assay)

The ELIFA procedure to determine quantitatively the amounts of $PrP^C$ and $PrP^{Sc}$ in given tissue homogenates has been described for hamster brain homogenates (Oesch et al., 1994). Blotting directly on nitrocellulose has the advantage over the conventional ELISA procedure that the poor solubility of bovine $PrP^{Sc}$ does not affect its immobilization on the solid phase. Blotting was performed with an ELIFA apparatus (Pierce), i.e. a peristaltic pump created a vacuum below the NC thereby sucking the contents of the wells above onto the NC in a controlled and highly reproducible way. Wells were then washed with PBS. The membrane was removed from the ELIFA apparatus, placed in a plastic tray and then incubated on a rocking table sequentially for the indicated times with the following reagents (inbetween steps, the filters were always washed 3× with PBS): 5% BSA/TBST (30 min), avidin (25 µg/ml, 30 min), biotin (2 µg/ml; 30 min); monoclonal antibodies 6H4 or 34C9 in TBST (2 h RT or 10 h o/n); secondary, biotinylated anti-mouse IgG (Vectastain, USA, dilution 1:5000, 1 h RT), streptavidin coupled to peroxidase (Boehringer, Germany, dilution 1:25000, 15-60 min RT)

In an alternative procedure, monoclonal antibodies 6H4 or 34C9 were biotinylated eliminating the step with the biotinylated secondary antibody. Still another procedure involved coupling of mABs 6H4 or 34C9 directly to peri-oxidase according to the manufacturer (Pierce, USA). Amplification of peroxidase activity was achieved by the BLAST-kit according to the manufacturer (DuPont, USA).

Subsequently, the NC was again placed in the ELIFA apparatus, a 96-well microtiterplate was placed underneath the membrane, such that each blotted spot corresponded to one well in that plate. Then the substrate TMB/peroxide (Kierkegaard & Perry) was applied into the wells of the ELIFA apparatus and sucked through the membrane into the wells of the microtiter plate. The reaction was stopped by the addition of 2M $H_3PO_4$. The extinction was measured at 450 nm with a reference at 620 nm in an ELISA reader.

Figure 3B:
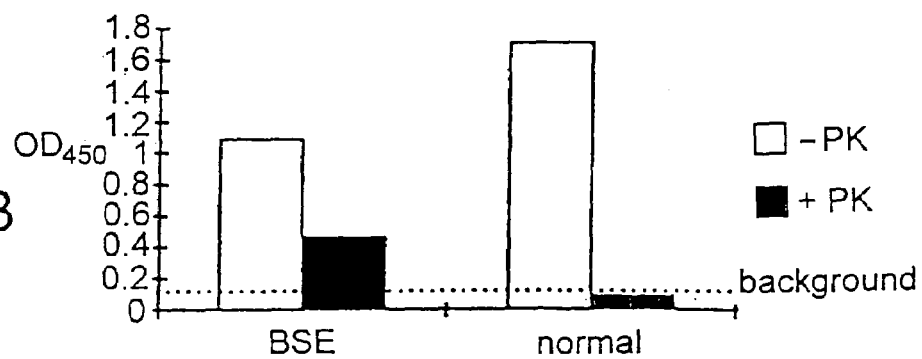

The standard curve for the ELIFA (see FIG. 3a) was obtained by serial dilutions of ultra-pure and defined amounts of recombinant bovine PrP (see below). For the ELIFA-procedure, lyophilized recombinant PrP was suspended in an antigen-dilution buffer (1M guanidinium thiocyanate and 0.01% human serum albumin in PBS). This buffer allows maximum binding of recombinant PrP to the nitrocellulose membrane. The standard curve is essential, since it allows to control both the quality and the reliability of the ELIFA-procedure. Furthermore, the standard curve allows to exactly quantify bovine $PrP^C/PrP^{Sc}$ amounts in given tissue specimens (Oesch et al., 1994) (FIG. 3b).

EXAMPLE 1.4.

Conventional ELISA (Enzyme Linked Immuno Sorbent Assay)

Figure 3C:
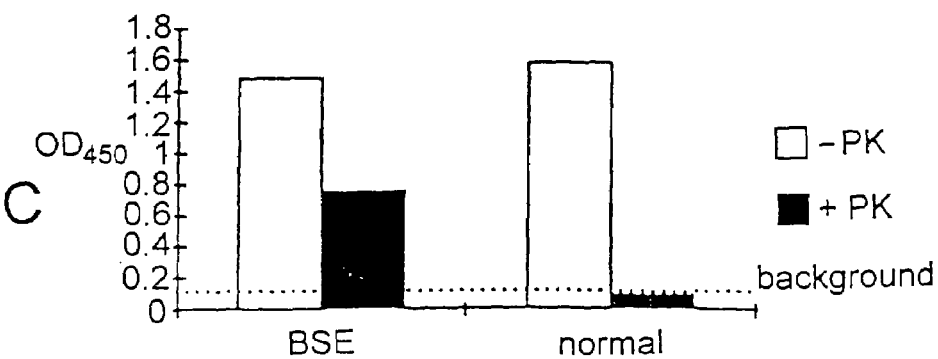

The antigen (present in a 10% homogenate as described in example 1.1.) was incubated for 2 h at RT in 96-well microtiterplates (Nunc, Denmark). Blocking was achieved with 5% BSA after antigen incubation. After washing, the plate was incubated with the biotinylated monoclonal antibody or 6H4 for 2 h at RT. Washing with $H_2O$ and PBS was performed before streptavidin-coupled peroxidase (Boehringer, Germany) was applied and peroxidase activity detected with the substrate according to the manufacturer (TMB/$H_2O_2$, Kierkegaard & Perry). The reaction was stopped by the addition of 2 M $H_3PO_4$. As for the ELIFA procedure, the plate is read by an ELISA reader at 450 nm with a reference at 620 nm. As an alterative procedure, peroxidase-coupled monoclonal antibody 6H4 was used instead of biotinylated antibody (see example 1.3.). Amplification of peroxidase activity was achieved by the ELAST-kit according to the manufacturer (DuPont USA). Results of this immunological test are depicted in FIG. 3c.

EXAMPLE 1.5.

Capture-ELISA (Enzyme Linked Immuno Sorbent Assay)

For the capture-ELISA, advantage can be taken of the multimeric nature of disease-specific $PrP^{Sc}$. Using the same monoclonal antibody for coating the wells and detection of native PrP (e.g. 6H4) will detect only PrP that exists in multimeric form or aggregated states, since monomeric PrP will have blocked its single binding site for the detection mAB by the coating mAB. Multimeric $PrP^{Sc}$ will be detected because apart from the one mAB binding site that couples the multimeric PrP to the microtiter plate, other binding sites are still present for the detection antibodies (see FIG. 4). This particular procedure of a capture-ELISA for $PrP^{Sc}$ detection can only be performed with the present monoclonal antibodies binding to native $PrP^{Sc}$, since upon denaturation the multimeric $PrP^{Sc}$ complexes dissociate into multiple monomeric, denatured PrP molecules.

For the capture ELISA, monoclonal antibodies according to the invention were either covalently linked or adsorbed to microtiterplates (Nunc, Denmark). Subsequently, the wells were blocked with 5% BSA for 30 min at RT and the procedure according to example 1.4. followed.

EXAMPLE 2

Experimental Details for the Production of Monoclonal Antibodies Specific for the Native and Denatured Prion Protein

EXAMPLE 2.1.

Preparation of the Immunogen

The following primers were chosen to amplify PrP DNA from bovine genomic DNA.

```
1 N-terminal sense primer
5'-GGGAATTCCATATGAAGAAGCGACCAAA      (SEQ ID NO: 3)
ACCTG-3'
and 2 C-terminal antisense primer
5'-CCGGGATCCTATTAACTTGCCCCTCGT       (SEQ ID NO4)
TGGTA-3'
```

These primers were designed to introduce an Nde I restriction site at the 5' end and a BamHI restriction site at the 3' end in the PCR-amplified bovine PrP-DNA. 10 cycles of 1 mm 94° C. 2 min 42° C. and 2 min 72° C. followed by 4×5 cycles of 1 min 94° C. 1 min 63° C. and 72° C. with augmenting durations of 1,2,3 and 4 min were performed in a Crocodile III thermocycler (Appligene, USA).

The PCR product then digested with the restriction enzymes Nde I and BamH I (Boehringer, Germany). The appropriate DNA fragment of 650 bp was purified on a 1% agarose gel and ligated into the pET11a vector (Novagen) previously digested with Nde I and BaMHI. Ligated products were transfected into E. coli strain DH5α. The appropriate clone containing the PrP open reading frame in the pET11a vector was selected and subsequently termed pbPrP3 (FIG. 5). Sequencing of the PrP sequence in pbPrP3 confirmed that the sequence of the bovine PrP gene in the pET11a vector corresponds to the previously published sequence (Goldmann et al., 1991; SEQ ID NO: 1). Plasmid pbPrP3 was transfected into *E. coli* strain BL21(DE3) (Novagen), that is capable of translating the plasmid into a protein. For production of bovine PrP, cells were stimulated with 1 mM IPTG according to standard techniques (Sambrook et al., 1989). Recombinant bovine PrP was purified from inclusion bodies. For example, 1 liter of Luria broth medium (Gibco, USA) containing 100 µg/ml ampicillin was incubated with an overnight culture (4 ml) of pbPrP3 transfected BL21(DE3) cells. The 1l culture was then grown at 37° C. and 250 rpm to an $OD_{600}$ of 0.8. IPTG was added to a final concentration of 1 mM and the incubation was continued at 30° C. and 250 rpm for 3 h until the $OD_{600}$ was 1.0. The culture was then centrifuged at 1000×g for 5 min at RT. The pellet containing the bacteria was further processed for isolation of PrP from inclusion bodies as follows: the bacterial pellet from a 1 liter culture was resuspended in 100 ml of 2 mM EDTA, 50 mMTris-HCl pH 7.5 and lysed by the addition of lysozyme (final concentration 100 mg/ml) and Triton-X-100 (final conc. 1%) for 15 min at 37° C. Then, $MgCl_2$ (final conc. 15 mM) and DNAse 1 (final conc. 10 µg/ml) were added, The suspension was shaken at room temperature until the DNA was digested and the solution was clear (30 min). The solution was then centrifuged at 10.000×g for 30 min at 4° C. The supernatant containing all the soluble proteins was discarded and the pellet, containing the inclusion bodies, was homogenized and resuspended in $1/10^{th}$ of the original culture volume containing 8M deionized urea, 10 nM MOPS ph 7.5. This suspension was then shaken at room temperature over night and then centrifuged at 1000×g for 30 min at 4° C. The supernatant containing solubilized material from inclusion bodies was then further processed.

A carboxymethyl (CM) sepharose column (Pharmacia) was equilibrated first with the elution buffer containing 8M deionized urea, 500 mM NaCl, 10 mM MOPS pH 7.5, then with the washing buffer containing 8M deionized urea, 10 mM MOPS pH 7. A CM sepharose column (50 ml bed volume) was loaded with 100 ml of the solution containing the solubilized proteins from inclusion bodies. The column was washed twice with 25 ml 50 mM NaCl, 8M urea 10 mM MOPS and once with 100 mM NaCl, 8M urea, 10 mM MOPS bovine recombinant PrP was eluted with 500 mM NaCl. 8M urea, 10 mM MOPS. SDS-PAGE and silver staining showed that at this step only one protein of about 24 kDa was present in the eluent, corresponding to the calculated molecular weight of 23.6 kDa (FIG. 6a) This fraction was then further processed.

Proteins eluted from the CM sepharose were subsequently either oxidized with 10 µM $Cu_2SO_4$ or reduced with 2% β-mercaptoethanol for several hours before they were loaded on a $C_4$-reverse phase HPLC column. The HPLC column was perfused with a 0-85% gradient of acetonitrile in 0.1% trifluoroacetic acid (TFA). The oxidized or reduced bovine recombinant PrP eluted about 40 or 45% acetonitrile, respectively, The eluted fractions were lyophilized (Sambrook et al., 1989) and redissolved in distilled water Electrospray mass spectroscopy revealed single peaks of 23676.8 and 23686.1 Dalton for oxidized and reduced recombinant bovine PrP, respectively, indicating a correct and uniform translation of the bovine PrP open reading frame in pbPrP3.

EXAMPLE 2.2

Immunization of Animals and Hybridoma Production

Oxidized or reduced bovine recombinant PrP or a mixture of both amounting to a total of 100 µg in a single dose (dissolved in PBS) were used to immunize $PrP^{0/0}$ mice, i.e. mice without a functional PrP genc (Bueler et. al. 1992) that were kindly provided by Prof. C Weissmann, University of Zurich. The reduced form of the recombinant PrP was particularly interesting since it has been reported to contain more β-sheet secondary structures than the oxidized form in a Syrian hamster recombinant PrP fragment (Alchlhorn et al. 1996), hence mimicking structural features of $PrP^{Sc}$, however, the reduced recombinant isoforms have been reported to be neither protease-resistant nor infectious (Mehlhorn et al. 1996).

Mice received three subcutaneous (day 0 with Freund's complete adjuvant, days 21 and 42 with Freund's incomplete adjuvans) of the antigens in a constant 100 µg amount and in a volume of 100 µl. On day 49, mice were boosted with the antigen intraperitoneally and the next day intravenously with adjuvant. Pertussi Berna (Berna Switzerland, extract of *Bordetella pertussis* bacteria). On day 50, mice were anesthetized and decapitated. The spleen front immunized mice was removed, and splenocytes were recovered. Mouse myeloma cells (cell line P3X63Ag8U.1. ATCC CRL 1597, Scharff, 1978) were mixed to the splenocytes at a ratio of 1:5 and fused by the addition of 50% PEG (polyethylenglycol) for 8 min at RT according to standard techniques (Kennett, 1980). Cells were then washed and grown overnight. The next day cells were suspended in selective medium (HAT) and plated in 96-well microtiterplates. The selective medium contains aminopterin that is toxic for those cells that have not been fused to splenocytes and thus eliminates uncontrolled cell growth of irrelevant cells (Kennett, 1980).

EXAMPLE 2.3

Screening Hybridomas for Specific Antibodies

Most important was an efficient screening method for antibody-producing hybridoma cell lines that would allow to detect monoclonal antibodies against native and denatured epitopes of both PrP isoforms, as well as conformation-specific epitopes of bovine $PrP^{Sc}$. The screening for hybridoma cells producing antibodies against PrP was done by an ELISA, Western blotting and a conformation-sensitive ELIFA.

ELISA using Recombinant Bovine PrP 96-well microtiter plates were coated with recombinant bovine PrP (0.25 µg/well) for 4 h at RT and then blocked with 5% $BSA/H_2O$ for 1 h at RT. After washing with $H_2O$ and PBS, culture medium from wells containing hybridoma colonies was transferred to the mictrotiter plates (50 µl per well) and incubated overnight at 4° C. After washing with $H_2O$ and PBS, bound antibodies were detected with a peroxidase-labeled anti- mouse IgG antibody ((appell, Switzerland) followed by colormetric detection with $1MB/H_2O$. (Kierkegaard & Perry, USA) as described in example 14.

Qualitative Conformation-sensitive ELIFA

1% brain homogenates of normal and BSE-infected cattle were either left undigested or protease-digested for the BSE brain homogenate and blotted onto a nitrocellulose membrane as described by for the ELIFA procedure (see above) (Oesch et al. 1994). After blotting, the membrane was blocked with 5% low-fat milk in TBST, and incubated with the antibody-containing culture medium. Subsequently, the NC was incubated with a secondary, peroxidase-coupled anti-mouse IgG antibody and developed with a chemiluminescence kit (ECL, Amersham). This technique allowed for detection of hybridoma cell lines that produce antibodies against native PrP$^C$ and bovine PrP$^{Sc}$ or of conformation-sensitive antibodies that distinguish between PrP$^C$ and bovine PrP$^{Sc}$(as described for mAB 15B3 in FIG. 6b).

Western Blotting

Hybridoma cell lines were further selected on the capability of the produced antibodies to recognize PrP of brain homogenates and recombinant bovine PrP on Western blots. Brain homogenates of various tissues and various species were blotted as described in example 1.2.

It was shown that the prefered monoclonal antibody 6H4 recognizes PrP in the brain homogenates of cattle, mice hamsters, pig, sheep and humans (FIG. 2).

The prefered mAB 34C9 recognizes PrP in the brain homogenates of cattle, mice, pig, and humans (FIG. 2).

Figure 1A:
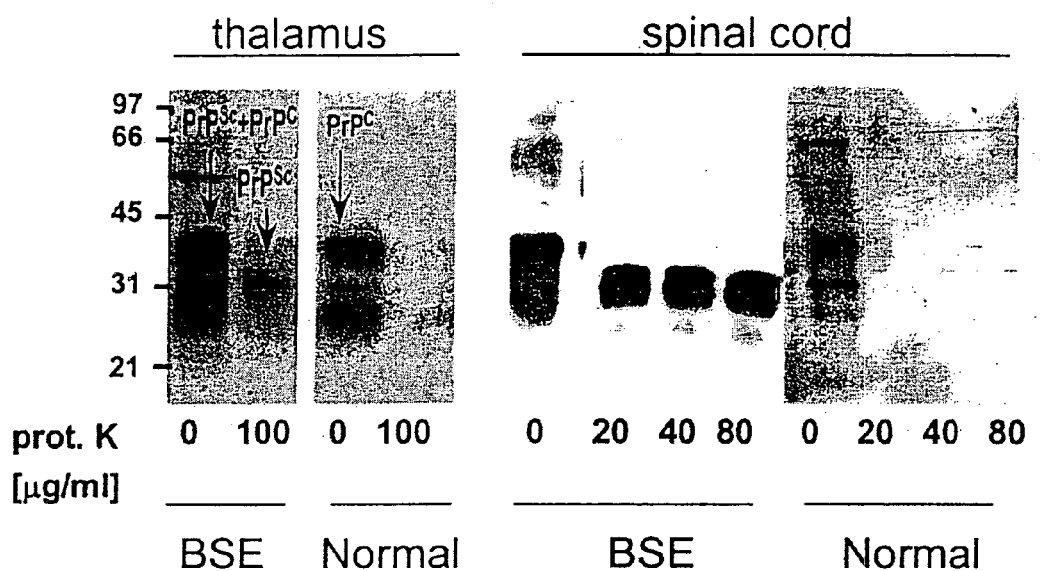
FIG. 1. a. Western blot of bovine PrP$^C$/PrP$^{Sc}$ without (0 µg) and after treatment with 20, 40, 80 or 100 µg/ml of proteinase K for 1 h at 37° C. The blot shows that bovine PrP$^{Sc}$ in homogenates from thalamus (left) and spinal cord (right of BSE-diseased and normal cattle is protease-resistant at several concentrations as compared to bovine PrP$^C$. Staining with mAB 6H4 followed by peroxidase-labelled anti-mouse IgG antibody. Peroxidase activity was detected by chemiluminescence.

It was further shown that both prefered monoclonal antibodies 6H4 and 34C9 recognize PrP in various tissues such as medulla, spinal cord, thalamus, cortex and white blood cells (FIGS. 1a, b).

Mapping of Epitopes

A peptide library consisting of 104 peptides numbered 1 to 104 purchased from Jerini Biotools (Berlin, Germany) was used to map the epitopes that are recognized by the antibodies. The peptides are covalently linked to a cellulose membrane have each a length of 18 amino acids and together cover the entire length of the recombinant bovine prion protein (total of 104), starting with Lys Lys Arg Pro Lys Pro Gly Gly Gly Trp Asn Thr Gly (one letter code, KKRPK-PGGGWNTG) and ending with Gln Arg Glu Ser Gln Ala Tyr Tyr Gln Arg Gly Ala Ser (one letter code QRESQAYYQRGAS). Each peptide overlaps by 11 amino acids with the next peptide. Binding of antibodies to those peptide can be visualized by the ECL system as described for Western blotting in example 1.2.

The monoclonal antibodies of the present invention bound to peptides comprised in the region of helix 1 in the three-dimensional model of the mouse recombinant C-terminal prion protein fragment described by Riek et al. (1996). It is hereby assumed that this mouse recombinant C-terminal prion protein fragment reflects structures of native PrP$^C$, has the same structure as full length PrP and that the structure will be similar in different species. Based on these assumptions the following statements are mAB 6H4 binds to the three library peptides Nos. 64 to 66, comprising amino acids 155-163 of the bovine PrP sequence (Asp Tyr Glu Asp Arg Tyr Tyr Arg Glu Goldmann et al., 1991 ) (FIG. 7b). This sequence corresponds exactly to the full-length helix, a structure that is highly conserved between species (Oesch et al., 1991).

mAB 34C9 binds to the 5 library peptides Nos. 59 to 63 comprising amino acids 149-153 of the bovine PrP sequence (Leu Ile His Phe Gly; Goldmann et al., 1991) (FIG. 7a) which corresponds to a sequence just N-terminal of helix 1 (Riek et al., 1996).

As predicted by this epitope mapping, the monoclonal antibodies differentially bind PrP from different species (FIG. 2).

Characterization of PrP$^{Sc}$ Conformation-specific Monoclonal Antibody 15B3 mAB 15B3 recognizes 3 distinct arrays of peptides: Nos. 62 to 65 of the peptide library comprising amino acids 153 to 159 (Gly Ser Asp Tyr Glu Asp Arg), Nos. 73 to 75 comprising amino acids 173 to 181 (Tyr Tyr Arg Pro Val Asp Gln Tyr Ser) and No 102 comprising amino acids 225 to 237 (Cys Ile Thr Gln Tyr Gln Arg Glu Ser Gln Ala Tyr Tyr) of bovine PrP according to Goldmann et al. (1991)

Figure 6A:
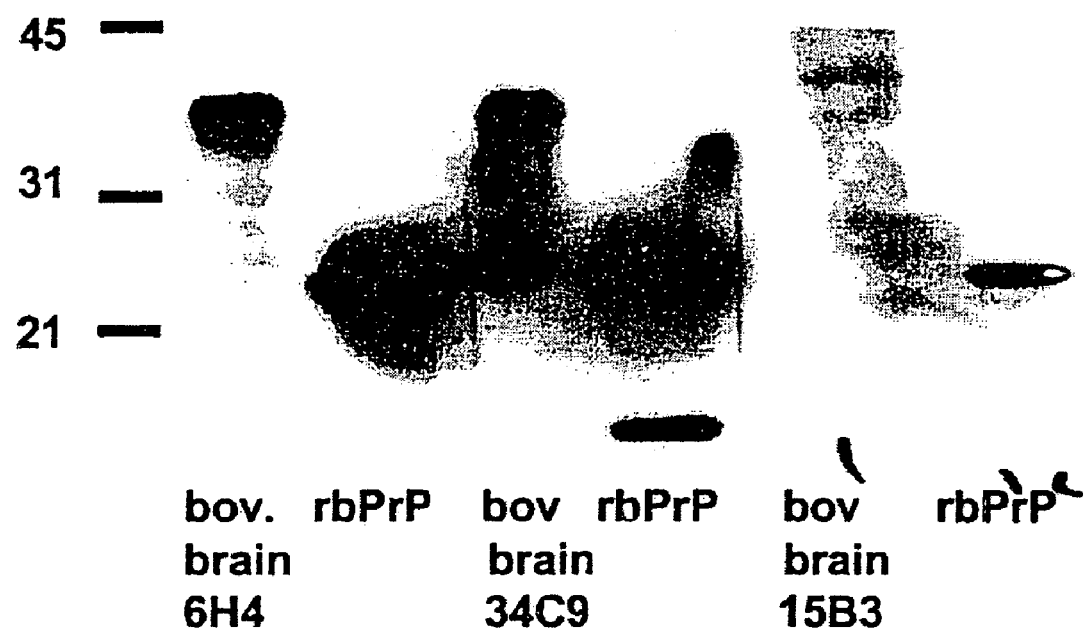
Figure 6B:
Figure 8A:
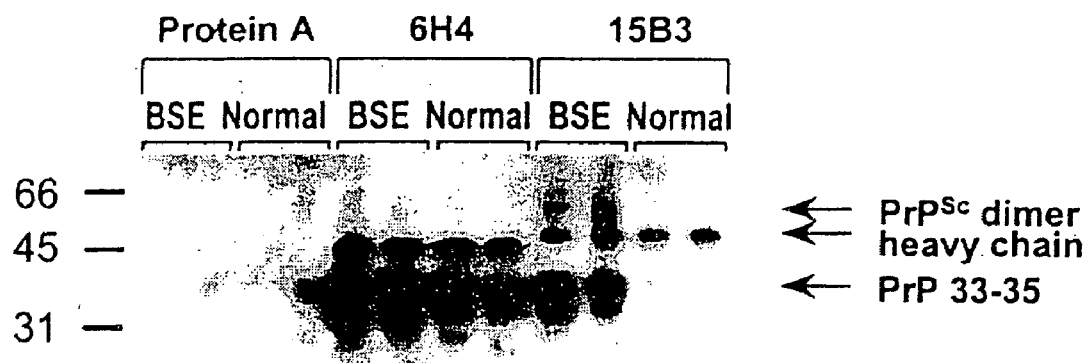
Figure 8B:
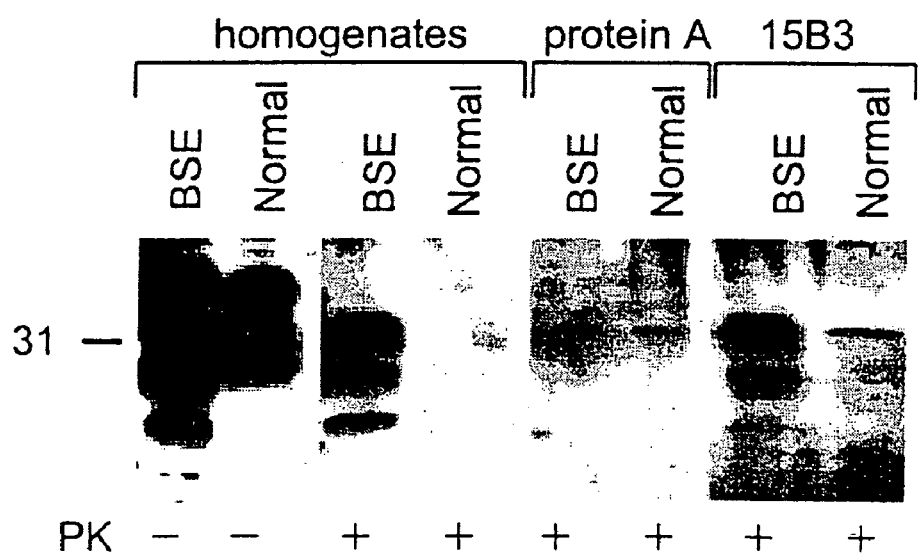
Figure 8C:
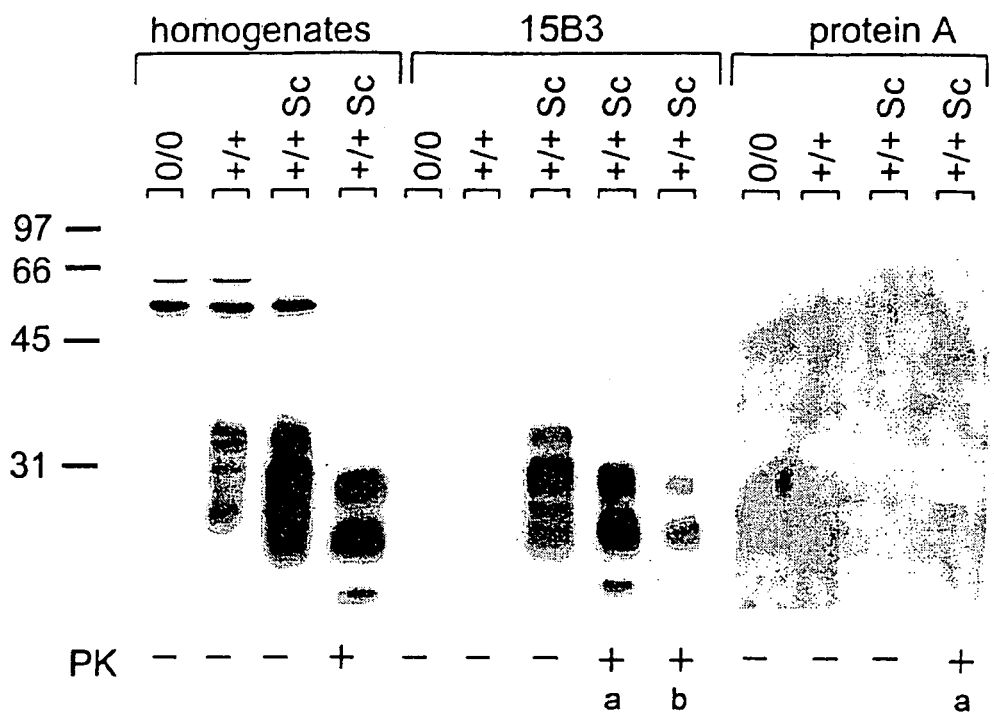
Figure 8D:
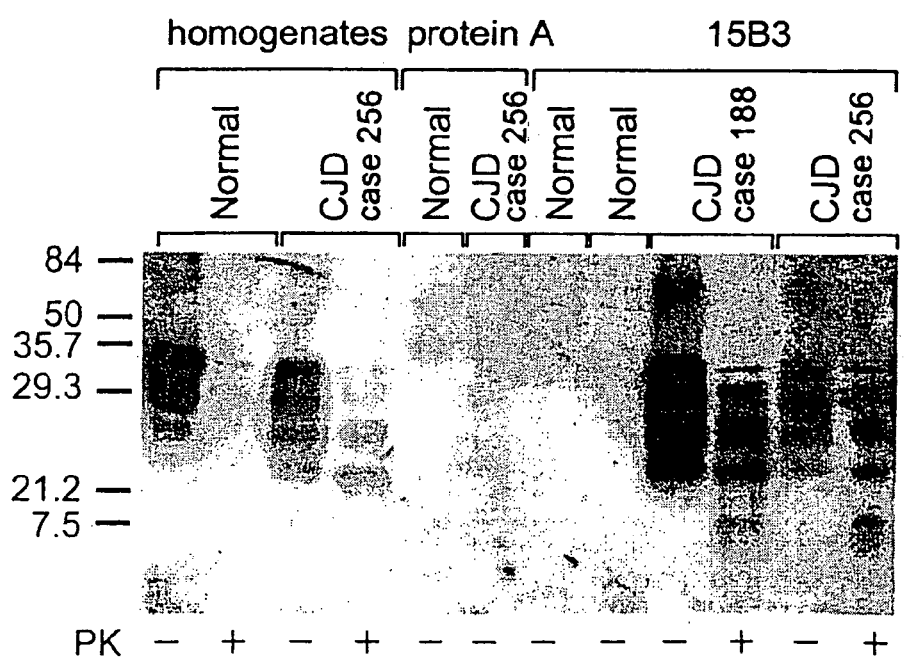

Monclonal antibody 15B3 recognizes native bovine PrPSc better than native bovine PrPC (FIG. 6b). In this experiment, 10% bovine brain homogenates of example undigested and BSE-diseased protease-digested cattle were made as described in example 1.1. Subsequently, the samples were diluted to a 0.5% homogenate with PBS and incubated at 37 °C. for 1 h. The samples were then blotted onto a nitrocellulose membrane with the qualitative conformation-sensitive ELIFA protocol as described in example 1 above. In FIG. 6b, it can be seen that 15B3 binds to BSE but not to normal brain homogenate. By Western blotting, PrP from bovine brain homogenates cannot be detected (FIG. 6a). Apparently mAB 15B3 cannot detect PrP on Western blotting even if it is assumed that proteins denature in sample buffer containing SDS before they are loaded on the gel (Example 1.2; Sambrook et al. 1989).

These findings point to the fact that mAB 15B3 binds to a conformation-sensitive epitope. As can be seen in the binding experiments with the peptide library, mAB 15B3 binds to several distant peptides as would be expected for a conformation-sensitive mAB.

Figure 1B:
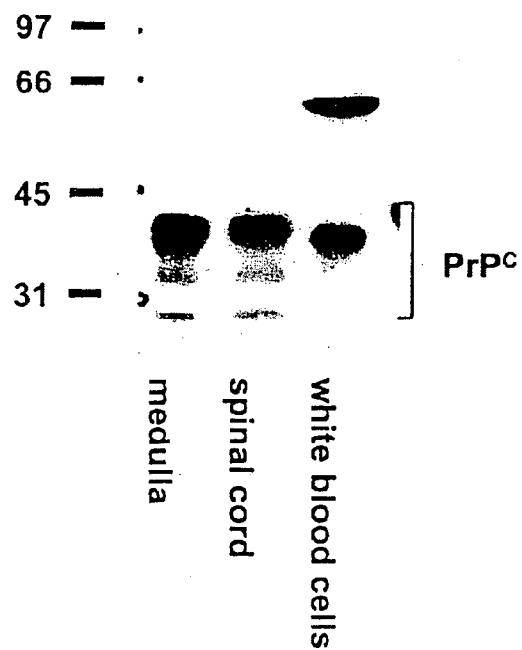

The specificity of the antibody 15B3 was further confirmed by immunoprecipitation (FIG. 8). While 6H4 precipitated PrP from normal as well as PrP$^{Sc}$-containing homogenates, 15B3 precipitated only PrP$^{Sc}$ from infected cattle, mice or humans (FIGS. 1A, C, D, respectively). The precipitated PrP was shown to be protease resistant (FIGS. 1B, C, D). For immunoprecipitation, 200 µl 1% brain homogenates were incubated for 2 h at room temperature with 200 µl 0.25 µg/ml antibody-containing serum-free medium, after incubation with additional 50 µl protein A- or protein G-coupled agarose (for 15B3 and 6H4, respectively; Boehringer Mannheim) for 2 h at room temperature, agarose beads were centrifuged and the pellet washed according to the manufacturer. Pelleted proteins were analyzed on Western blots.

EXAMPLE 3

Reduction of Infectivity of Prions by Monoclonal Antibodies

Brain homogenates from BSE-infected cattle are obtained as described in example 1.1 The exact amount of present bovine PrP$^{Sc}$ are measured with the help of the ELIFA technique or the ELISA technique as described in examples 1.3 to 1.5. respectively. Serial dilutions of this infected brain homogenate are aliquoted. To these serial dilutions are added the preferred mABs 6H4 or 34C9 or 15B3. or a mixture thereof, in molar amounts exceeding the molar amounts of measured PrP$^{Sc}$. The mix is incubated for 4 h at RT and then 100 µl are injected intracerebrally into the animal. Transgenic mice overexpressing mouse PrP (tg35; Fischer et al. 1996) are used as an animal model for measuring the infectivity of bovine PrP$^{Sc}$.

List of Buffers and Solutions

HT-medium
  450 ml Iscove's modified Dulbecco's medium (GIBCO)
  30 ml sterile human serum
  5 ml glutamine (200 mM)
  5 ml hypoxanthine (10 mM)/thymidine (1.5 mM)
  5 ml penicilin (10000 IU/ml)/streptomycin (10000 μg/ml)
  250 μl sterile β-mercaptoethanol HAT-medium
  HT-medium+2 mM aminopterin TBS
  20 mM Tris pH 7.5
  150 mM NaCl
  0.05% Tween 20

TBST
  20 mM Tris pH 7,5
  150 mM NaCl
  0.05% Tween 20

Deposit or Microorganisms

The hybridoma cell lines were deposited under the Budapest Treaty at the Deutsche Sammlung von Mikroorganismen und Zellkulturen GmbH, Mascheroder Weg Ib, D-381324 Braunschweig, as follows:
1. Hybridoma cell line producing mAB 34C9: DSM ACC2295, deposited Feb. 06, 1997
2 Hybridoma cell line producing mAB 6H4: DSM ACC2296, deposited Feb. 06, 1997
3 Hybridoma cell line producing mAB 15B3: DSM ACC2298, deposited Feb. 13, 1997

---

The invention claimed is:

1. An antibody producing hybridoma cell line deposited under DSM ACC2295.

2. An isolated monoclonal antibody produced by the hybridoma cell line according to claim 1 or a fragment of said antibody, wherein the fragment binds SEQ ID NO: 6.

3. An isolated monoclonal antibody which comprises an epitope binding fragment of the monoclonal antibody according to claim 1 wherein the epitope binding fragment binds SEQ ID NO: 6.

4. An isolated monoclonal antibody according to claim 1 coupled to other molecules including fragments of other antibodies, enzymes or organic chemical compounds.

5. A method for the production of an antibody according to claim 1, comprising culturing a hybridoma cell line according to claim 1 and isolating the monoclonal antibody from the supernatant.

* * * * *

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 660 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Bos taurus
      (D) DEVELOPMENTAL STAGE: Adult (vii) IMMEDIATE SOURCE:
      (B) CLONE: pbPrP3

(xi) SEQUENCE DESCRIPTION: SEQ ID NO: 1:

```
ATGAAGAAGC GACCAAAACC TGGAGGAGGA TGGAACACTG GGGGGAGCCG ATACCCAGGA      60

CAGGGCAGTC CTGGAGGCAA CCGTTATCCA CCTCAGGGAG GGGGTGGCTG GGGTCAGCCC     120

CATGGAGGTG GCTGGGGCCA GCCTCATGGA GGTGGCTGGG GCCAGCCTCA TGGAGGTGGC     180

TGGGGTCAGC CCCATGGTGG TGGCTGGGGA CAGCCACATG GTGGTGGAGG CTGGGGTCAA     240

GGTGGTACCC ACGGTCAATG GAACAAACCC AGTAAGCCAA AAACCAACAT GAAGCATGTG     300

GCAGGAGCTG CTGCAGCTGG AGCAGTGGTA GGGGGCCTTG GTGGCTACAT GCTGGGAAGT     360

GCCATGAGCA GGCCTCTTAT ACATTTTGGC AGTGACTATG AGGACCGTTA CTATCGTGAA     420

AACATGCACC GTTACCCCAA CCAAGTGTAC TACAGGCCAG TGGATCAGTA TAGTAACCAG     480

AACAACTTTG TGCATGACTG TGTCAACATC ACAGTCAAGG AACACACAGT CACCACCACC     540

ACCAAGGGGG AGAACTTCAC CGAAACTGAC ATCAAGATGA TGGAGCGAGT GGTGGAGCAA     600

ATGTGCATTA CCCAGTACCA GAGAGAATCC CAGGCTTATT ACCAACGAGG GGCAAGTTAA     660
```

(2) INFORMATION FOR SEQ ID NO: 2:

(i) SEQUENCE CHARACTERISTICS:
      (A) LENGTH: 219 amino acids
      (B) TYPE: amino acid
      (C) STRANDEDNESS: single (D) TOPOLOGY: linear (ii) MOLECULE TYPE: protein (iii) HYPOTHETICAL: YES (iv) ANTI-SENSE: NO (vi) ORIGINAL SOURCE:
        (A) ORGANISM: Bos taurus (xi) SEQUENCE DESCRIPTION: SEQ ID NO: 2:

```
Met Lys Lys Arg Pro Lys Pro Gly Gly Gly Trp Asn Thr Gly Gly Ser
1               5                   10                  15

Arg Tyr Pro Gly Gln Gly Ser Pro Gly Gly Asn Arg Tyr Pro Pro Gln
            20                  25                  30

Gly Gly Gly Gly Trp Gly Gln Pro His Gly Gly Gly Trp Gly Gln Pro
            35                  40                  45

His Gly Gly Gly Trp Gly Gln Pro His Gly Gly Gly Trp Gly Gln Pro
50                  55                  60

His Gly Gly Gly Trp Gly Gln Pro His Gly Gly Gly Gly Trp Gly Gln
65                  70                  75                  80

Gly Gly Thr His Gly Gln Trp Asn Lys Pro Ser Lys Pro Lys Thr Asn
                85                  90                  95

Met Lys His Val Ala Gly Ala Ala Ala Gly Ala Val Val Gly Gly
            100                 105                 110

Leu Gly Gly Tyr Met Leu Gly Ser Ala Met Ser Arg Pro Leu Ile His
            115                 120                 125

Phe Gly Ser Asp Tyr Glu Asp Arg Tyr Tyr Arg Glu Asn Met His Arg
            130                 135                 140

Tyr Pro Asn Gln Val Tyr Tyr Arg Pro Val Asp Gln Tyr Ser Asn Gln
145                 150                 155                 160

Asn Asn Phe Val His Asp Cys Val Asn Ile Thr Val Lys Glu His Thr
            165                 170                 175

Val Thr Thr Thr Thr Lys Gly Glu Asn Phe Thr Glu Thr Asp Ile Lys
            180                 185                 190

Met Met Glu Arg Val Val Glu Gln Met Cys Ile Thr Gln Tyr Gln Arg
            195                 200                 205

Glu Ser Gln Ala Tyr Tyr Gln Arg Gly Ala Ser
            210                 215
```

(2) INFORMATION FOR SEQ ID NO: 3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: NO (xi) SEQUENCE DESCRIPTION: SEQ ID NO: 3:

GGGAATTCCA TATGAAGAAG CGACCAAAAC CTG                                33

(2) INFORMATION FOR SEQ ID NO: 4:

(i) SEQUENCE CHARACTERISTICS:

(A) LENGTH: 31 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide"

(iii) HYPOTHETICAL: NO (iv) ANTI-SENSE: NO (xi) SEQUENCE DESCRIPTION: SEQ ID NO: 4:

CGGGATCCTA TTAACTTGCC CCTCGTTGGT A                                31

(2) INFORMATION FOR SEQ ID NO: 5:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: peptide (iii) HYPOTHETICAL: YES (iv) ANTI-SENSE: NO (xi) SEQUENCE DESCRIPTION: SEQ ID NO: 5:

Leu Ile His Phe Gly
1               5

(2) INFORMATION FOR SEQ ID NO: 6:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (iii) HYPOTHETICAL: YES (iv) ANTI-SENSE: NO (xi) SEQUENCE DESCRIPTION: SEQ ID NO: 6:

Asp Tyr Glu Asp Arg Tyr Tyr Arg Glu
1               5

(2) INFORMATION FOR SEQ ID NO: 7:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (iii) HYPOTHETICAL: YES (iv) ANTI-SENSE: NO (xi) SEQUENCE DESCRIPTION: SEQ ID NO: 7:

Gly Ser Asp Tyr Glu Asp Arg
1               5

(2) INFORMATION FOR SEQ ID NO: 8:

-continued

```
    (i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (xi) SEQUENCE DESCRIPTION: SEQ ID NO: 8:

Tyr Tyr Arg Pro Val Asp Gln Tyr Ser
1               5

(2) INFORMATION FOR SEQ ID NO: 9:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (xi) SEQUENCE DESCRIPTION: SEQ ID NO: 9:

Cys Ile Thr Gln Tyr Gln Arg Glu Ser Gln Ala Tyr Tyr
1               5                   10
```